United States Patent [19]

Hatano et al.

[11] Patent Number: 4,906,663
[45] Date of Patent: Mar. 6, 1990

[54] 6-FLUOROPROSTAGLANDINS

[75] Inventors: Naonobu Hatano, Takaishi; Buichi Fujitani, Sakai; Toshiaki Kadokawa, Hirakata; Yasushi Matsumura, Yokohama; Tomoyuki Asai, Yokohama; Arata Yasuda, Yokohama; Keiichi Uchida, Kawasaki, all of Japan

[73] Assignees: Asahi Glass Company, Ltd., Tokyo; Dainippon Pharmaceutical Company, Ltd., Osaka, both of Japan

[21] Appl. No.: 257,808

[22] Filed: Oct. 14, 1988

[30] Foreign Application Priority Data

Oct. 16, 1987 [JP] Japan ................. 62-259649

[51] Int. Cl.$^4$ ............... C07C 177/00; A61K 31/557
[52] U.S. Cl. ............................. 514/530; 514/573; 560/121; 562/503
[58] Field of Search ............... 560/121; 562/503; 514/530, 573

[56] References Cited

U.S. PATENT DOCUMENTS 4,699,989 10/1987 Arata ................. 550/441

FOREIGN PATENT DOCUMENTS

WO8101002 4/1981 PCT Int'l Appl. .......... 514/530

OTHER PUBLICATIONS

Nakai, Chem. Lett., 1979, 1499.
Chemistry Letters, 1979, pp. 1499–1502, The Chemical Society of Japan, Nakai et al.: Synthesis of 5-fluoro--prostaglandins.

Primary Examiner—Robert Gerstl
Attorney, Agent, or Firm—Oblon, Spivak, McClelland, Maier & Neustadt

[57] ABSTRACT

A 6-fluoroprostaglandin having the formula:

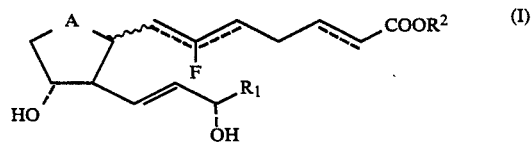

wherein A is a carbonyl group or a hydroxymethylene group, $R^1$ is a substituted or unsubstituted $C_1$–$C_{10}$ alkyl group or a substituted or unsubstituted 5- or 6-membered cycloalkyl group, $R^2$ is a hydrogen atom or a $C_1$–$C_{10}$ alkyl group, each of $R^3$ and $R^4$ which may be the same or different is a hydrogen atom or a protecting group, $R^5$ is a hydrogen atom or a hydroxyl group, and ==== is a single bond or a double bond, and its salt when $R^2$ is a hydrogen atom.

8 Claims, No Drawings

6-FLUOROPROSTAGLANDINS

The present invention relates to prostaglandins having a fluorine atom at the 6-position.

Prostaglandins (hereinafter sometimes referred to simply as PG) have various important pharmacological activities, and a number of researches and developments have been made on various artificially modified porducts to practically develop them as drugs (Terashima et al, "Prostaglandins and related physiologically active substances" by Kodansha Scientific (1981)). For example, it has been reported recently that by the oxo-conversion of the 6-position of PG, an improvement in the pharmacological effects is observed ("Eur. J. Pharmacol.", vol. 60, 245 (1979)). However, in view of difficulties involved in the technical aspect of the modification of this 6-position, little derivatives have actually been developed. On the other hand, PG is a very unstable compound. Improvement of the stability of PG is, therefore, strongly desired to make PG useful in a wide range as drugs. For this purpose, it has been proposed to introduce fluorine to various positions ("Yuki Gosei Gyokaishi", vol. 42, 794 (1984)). However, no case has been reported for the introduction to the 6-position.

As a result of extensive researches, the present inventors have found that when a fluorine atom is introduced to the 6-position of PG, it is possible to obtain a strong antiplatelet effect, antianginal effect and inhibitory effect on gastric ulcer, and the stability of the product is high. The present invention has been accomplished on the basis of this discovery.

The present invention is concerned with a 6-fluoroprostaglandin (hereinafter sometimes referred to simply as 6-F-PG). More particularly, the present invention is concerned with a 6-fluoroprostaglandin having the formula I and its salts:

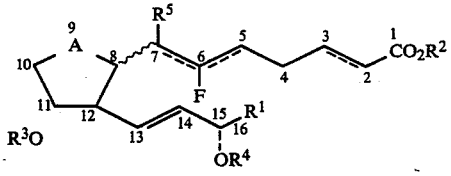

wherein A is a carbonyl group or a hydroxymethylene group, $R^1$ is a substituted or unsubstituted $C_1-C_{10}$ alkyl group or a substituted or unsubstituted 5- or 6-membered cycloalkyl group, $R^2$ is a hydrogen atom or a $C_1-C_{10}$ alkyl group, each of $R^3$ and $R^4$ which may be the same or different is a hydrogen atom or a protecting group, $R^5$ is a hydrogen atom or a hydroxyl group, and ==== is a single bond or a double bond.

Now, the present invention will be described in detail with reference to the preferred embodiments.

In 6-F-PG of the present invention represented by the formula I, $R^1$ is a substituted or unsubstituted $C_1-C_{10}$ alkyl group or a substituted or unsubstituted 5- or 6-membered cycloalkyl group. The $C_1-C_{10}$ alkyl group is preferably methyl, ethyl, n-propyl, iso-propyl, n-butyl, n-pentyl, n-hexyl, 1,1-dimethylentyl, 2-methyl-1-hexyl, 1-methyl-3-pentinyl or 1-methyl-3-hexynyl. The substituted or unsubstituted 5- or 6-membered cycloalkyl group is preferably a cyclohexyl group or a cyclopentyl group, or a cyclohexyl or cyclopentyl group which is substituted by e.g. methyl, ethyl, propyl, butyl, pentyl, phenoxy, trifluoromethyl or trifluoromethylphenoxy.

Particularly preferred as $R^1$ is a straight chain or branched $C_4-C_{10}$ alkyl group.

$R^2$ is a hydrogen atom or a $C_1-C_{10}$ alkyl group. The $C_1-C_{10}$ alkyl group (hereinafter represented by $R^{2'}$) may be a straight chain or branched alkyl group such as methyl, ethyl, n-propyl, iso-propyl, n-butyl, n-pentyl or n-hexyl. Among them, methyl and ethyl are preferred as $R^{2'}$.

Each of $R^3$ and $R^4$ which may be the same or different is a hydrogen atom or a protecting group. As the protecting group (hereinafter represented by $R^{3'}$ or $R^{4'}$), various prtecting groups may be employed. For example, it may be a silyl group having three substituents such as alkyl groups, aryl groups or aralkyl groups, an alkanoyl group, a tetrahydropyranyl group, a tetrahydrofuranyl group, a benzoyl group or a methoxyethoxy group.

Preferred is a trialkylsilyl group wherein the trialkyl groups may be the same or different. Particularly preferred is a trialkylsilyl group wherein at least one alkyl group is an alkyl group having at least two carbon atoms. Specifically, a dimethyl-t-butylsilyl group, a triethylsilyl group or a diphenyl-t-butyl group may be mentioned. Particularly preferred is a dimethyl-t-butylsilyl group.

A is a carbonyl group or a hydroxymethylene group.
==== represents a single bond or a double bond. However, the bond between the 5- and 6-positons and the bond between the 6- and 7-positions are not simultaneously double bonds. Preferably, the α-chain contains at most one double bond.

The compound of the present invention represented by the formula I has asymmetric carbon atoms at the 6-position (when the carbon-carbon bonds between the 5- and 6-positions and between the 6- and 7-positions are both single bonds), the 7-position, the 8-position, the 9-position (when A is a hydroxymethylene group), the 11-position, the 12-position and the 15-position. Therefore, it has various stereo isomers. The compound of the present invention includes all of such stereo isomers, optical isomers and mixtures thereof. Among the compounds of the formula I, those wherein both $R^3$ and $R^4$ are hydrogen atoms, will be represented by the formula I'.

The compound of the present invention represented by the formula I may be prepared, for example, by the following process.

(A): Of 6-F-PGE represented by the following formula II, the carbonyl group at the 9-position is optionally reduced, or the α-chain double bond is selectively reduced, and, if necessary, a double bond is introduced to the 2- and 3-positions, or the removal of protecting groups, the hydrolysis or the formation of a salt is conducted, to obtain a compound of the formula I.

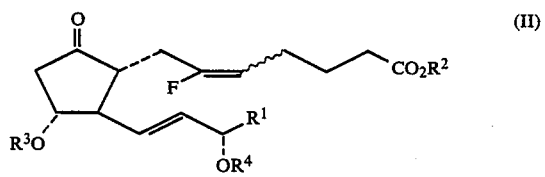

wherein $R^1$, $R^2$, $R^3$ and $R^4$ are as defined in the formula I. Further, in the reaction for reducing the carbonyl group or the double bond or for introducing a double bond, $R^2$, $R^3$ and $R^4$ are usually required to be $R^{2'}$, $R^{3'}$ and $R^{4'}$, respectively.

Here, the compound of the formula II can be prepared basically by the three methods (methods (a), (b) and (c)) as shown in scheme 1. However, in the following reactions, R² is usually required to be an alkyl group as R²′, and R³ and R⁴ are usually required to be protecting groups as R³′ and R⁴′, respectively.

Scheme 2

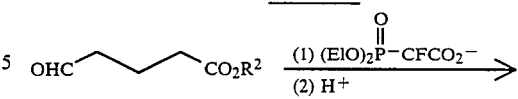

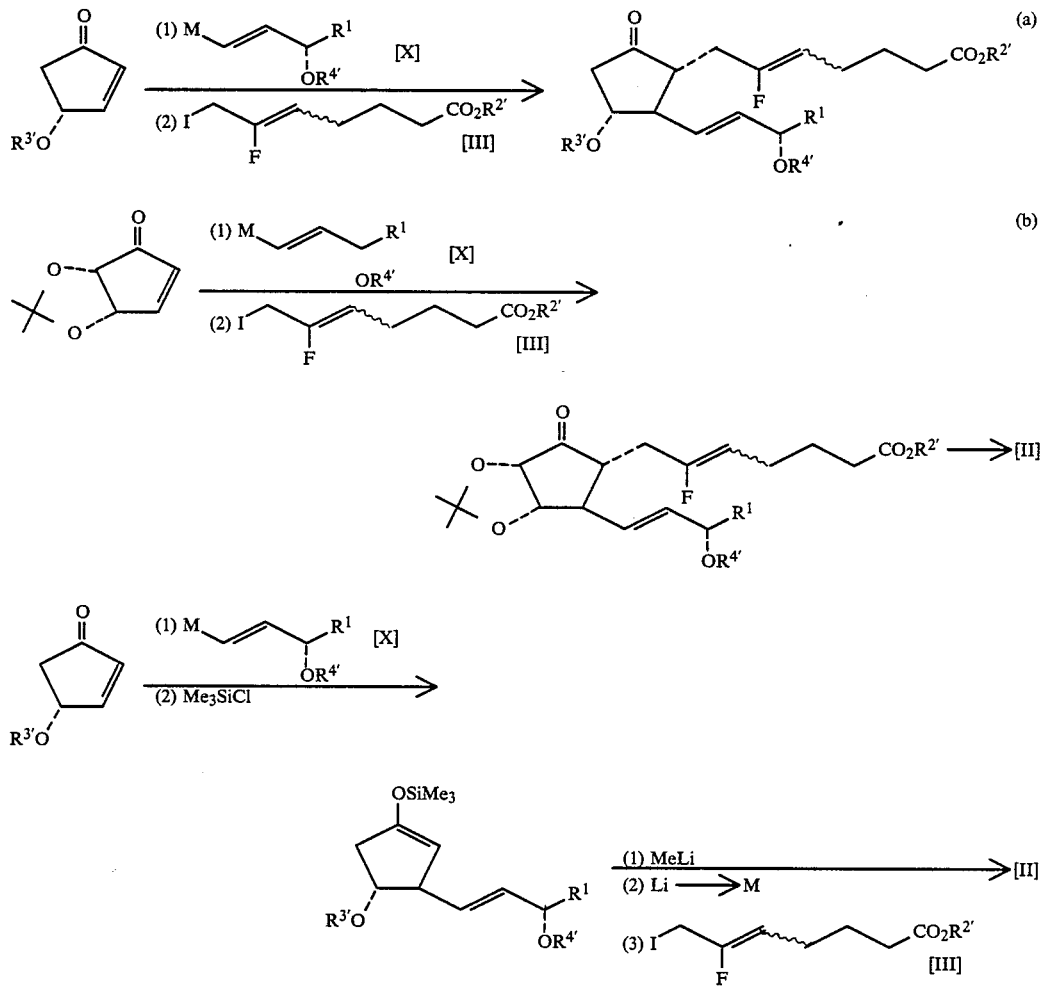

In the above formulas, M is an organic metal species such as copper, nickel, zirconium, zinc or aluminum, and R¹, R²′, R³′ and R⁴′ are as defined above with respect to the formula I.

The methods of the formulas (a) and (b) are disclosed in the literatures ("J. Am. Chem. Soc.", vol. 107, 3348 (1985) and "J. Am. Chem. Soc.", vol. 108, 5655 (1986)). In the formula (c), the technique of reacting an alkenyl metal reactant to an enone for 1,4-addition and introducing a trimethylsilyl group, is known ("J. Am. Chem. Soc.", vol. 97, 107 (1975)). The silylenol ether thereby obtained can be converted to the compound of the formula II by a known method ("J. Am. Chem. Soc.", vol. 95, 3310 (1973)).

The iodide compound of the formula III to be used here, is a novel compound. There is no particular restriction as to the manner for the preparation of this compound. However, this compound can be synthesized by the method shown by the following scheme 2.

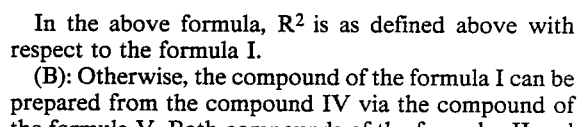

In the above formula, R² is as defined above with respect to the formula I.

(B): Otherwise, the compound of the formula I can be prepared from the compound IV via the compound of the formula V. Both compounds of the formulas II and IV will be represented by the formula II′.

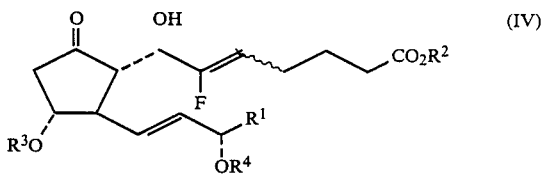

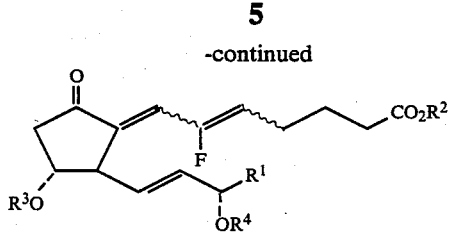

In the above formulas, $R^1$, $R^2$, $R^3$ and $R^4$ are as defined above with respect to the formula I. Further, during the synthesis, $R^2$, $R^3$ and $R^4$ are usually required to be $R^{2'}$, $R^{3'}$ and $R^{4'}$, respectively.

Here, there is no particular restriction as to the synthesis of the compound of the formula IV. However, it can be prepared by the two methods (methods (d) and (e)) shown by the following scheme 3.

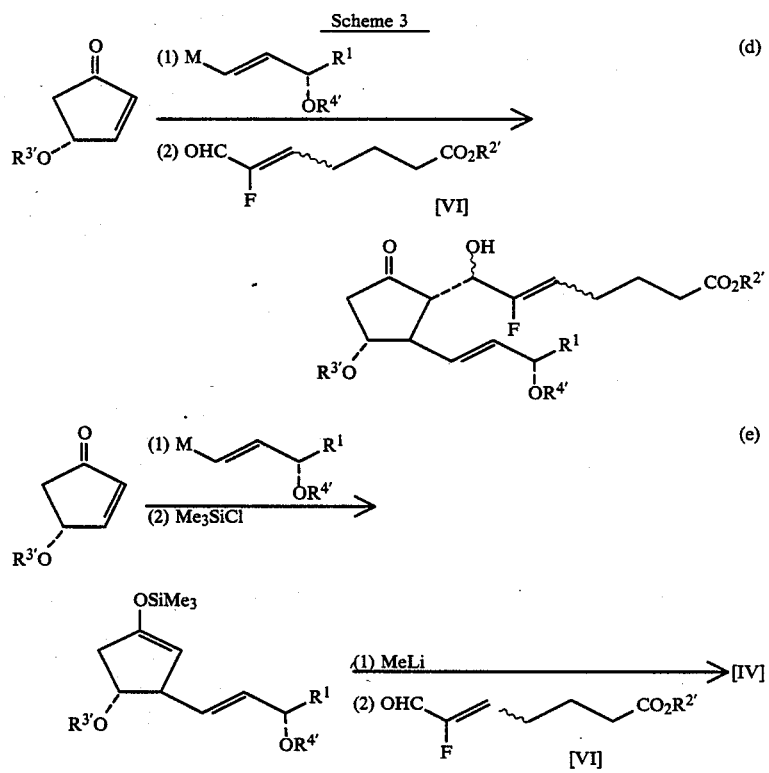

above-mentioned iodide of the formula III and the fluoroaldehyde of the formula VI will be represented by the fluorocarboxylic acid of the following formula IX.

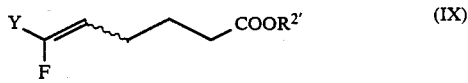

wherein Y is —$CH_2I$ or —CHO.

Scheme 4

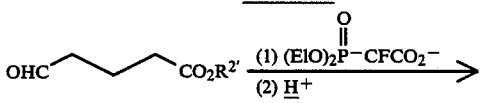

(d)

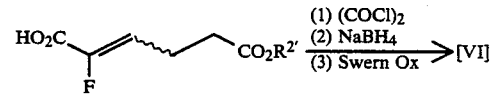

In the above formulas, M is an organic metal species such as copper, nickel, zirconium, zinc or aluminum, and $R^1$, $R^{2'}$, $R^{3'}$ and $R^{4'}$ are as defined above with respect to the formula I.

Here, the method of the formula (d) can be conducted in accordance with the method disclosed in a literature ("Tetrahedron Lett.", vol. 23, 4057 (1982)). In the method of the formula (e), as in the case of the above described (A)-(c), an alkenyl metal reactant is reacted to an enone for 1,4-addition and a trimethylsilyl group is introduced, by a conventional technique ("J. Am. Chem. Soc.", vol. 97, 107 (1975)), and then the product is converted to a compound of the formula VI in accordance with a known technique ("J. Am. Chem. Soc.", vol. 95, 3310 (1975)).

The fluoroaldehyde of the formula VI to be used here, is a novel compound. There is no particular restriction as to the manner for the preparation of this compound. However, it can be prepared by a method shown by the following flow chart (Scheme 4). The In the above formula, $R^{2'}$ is as defined above with respect to the formula I.

The compound of the formula IV is reacted with a reactive derivative of an organosulfonic acid in the presence of a basic compound to obtain a corresponding 7-organosulfonyloxy PG derivative, which is then treated with a basic compound to obtain the compound of the formula V.

The basic compound to be used here, is preferably an amine. Such an amine includes, for example, 4-methylaminopyridine, triethylamine, diisopropylcyclohexylamine, isopropyldimethylamine and diisopropylethylamine. Among them, 4-dimethylaminopyridine is particularly preferred.

The reactive derivative of organosulfonic acid may be, for example, a halide of organosulfonic acid such as methanesulfonyl chloride, ethanesulfonyl chloride, trifluoromethanesulfonyl chloride, benzenesulfonyl chloride or p-toluenesulfonyl chloride; or an organosulfonic acid anhydride such as methanesulfonic acid anhydride, ethanesulfonic acid anhydride, trifluoromethanesulfonic acid anhydride, benzenesulfonic acid anhydride or p-toluenesulfonic acid anhydride. Among them, methanesulfonyl chloride, p-toluenesulfonyl chloride and ethanesulfonic acid anhydride are particularly preferred.

As the solvent to be used for the reaction, the abovementioned basic compound may be used by itself. However, as the solvent, it is preferred to employ a halogenated hydrocarbon such as dichloromethane, chloroform or carbon tetrachloride; an ether such as ethyl ether or tetrahydrofuran; or a hydrocarbon such as benzene, toluene, pentane, hexane or cyclohexane. Particularly preferred is dichloromethane.

For the actual reaction, the reactive derivative of organosulfonic acid is used usually in an amount of from 0.5 to 20 mols, preferably from 2 to 5 mols per mol of the compound of the formula IV. The basic compound is used usually in an amount of from 1 to 20 mols, preferably from 4 to 10 mols, per mol of the compound of the formula IV.

The reaction temperature varies depending upon the types of the starting materials and the reagents. However, it is usual to conduct the reaction within a range of from 0° to 50° C., preferably from 10° to 30° C.

The 7-organosulfonyloxy PG derivative thus obtained, is then treated with a basic compound and converted to the compound of the formula V. The basic compound to be used here, may be the same compound as used in the above reaction for the 7-organosulofonyloxy PG derivative. The reaction can also be conducted under substantially the same reaction conditions. Namely, the 7-sulfonyloxy PG derivative may be isolated and then converted to the compound of the formula V by the removal of the 7-organosulfonyloxy group. Otherwise, the conversion may be conducted in the same reaction system without isolating the 7-sulfonyloxy PG derivative.

The compound of the formula V thus obtained, is then subjected to reduction to convert it to a mixture of 6-F-PGE$_2$ (a compound of the formula I wherein A is a carbonyl group and the 5-position is a double bond) and $\Delta^6$-F-PGE$_1$ (the compound of the formula I wherein A is a carbonyl group and the 6-position is a double bond, which includes a stereo isomer at the 8-position). This reduction reaction can be conducted preferably by the reduction by means of a zinc-type reducing agent such as zinc powder, zinc-silver or zinc-copper. In the reduction by means of such a zinc-type reducing agent, the reaction is conducted preferably in the presence of acetic acid. The zinc type reducing agent is used usually in an amount of from 1 to 500 mols, preferably from 5 to 100 mols, per mol of the starting material compound of the formula V, and acetic acid is used usually in an amount of from 1 to 2,000 mols, preferably from 10 to 1,000 mols, per mol of the starting material. As the solvent to be used for this reaction, an alcohol such as methanol, ethanol or isopropanol, dimethoxyethane, dimethylformmaide, dimethylsulfoxide, acetic acid or a solvent mixture thereof is preferably employed. Particularly preferred is methanol, isopropanol or acetic acid. The reaction temperature varies depending upon the starting materials and the reagents used. However, it is usual to conduct the reaction within a range of from the 0° to 120° C., preferably from 10° to 80° C. Further, it is possible to obtain $\Delta^6$-F-PGF$_1$ (a compound of the formula I wherein A is a hydroxymethylene group and the 6-position is a double bond) by reacting a 7,9-diol of the formula IV wherein the ketone group at the 9-position is reduced, with 1,1'-thiocarbonyldiimidazole in the presence of a basic compound to obtain a thiocarbonate compound, which is then subjected to a selective reduction.

The basic compound used to obtain this thiocarbonate compound, is preferably an amine. Such an amine includes, for example, 4-dimethylaminopyridine, triethylamine, diisopropylcyclohexylamine, isopropyldimethylamine and diisopropylethylamine. Among them, 4-dimethylaminopyridine is preferred.

As the solvent to be used for the reaction, the abovementioned basic compound may be used by itself. However, as the solvent, it is preferred to use a nitrile such as acetonitrile, a halogenated hydrocarbon such as dichloromethane, chloroform or carbon tetrachloride, or an ether such as ethyl ether or tetrahydrofuran. Particularly preferred is acetonitrile.

For the actual reaction, the reactive derivative of organosulfonic acid is used usually in an amount of from 0.5 to 20 mols, preferably from 1 to 3 mols, per mol of the diol. The basic compound is used usually in an amount of from 1 to 20 mols, preferably from 4 to 10 mols per mol of the diol.

The reaction temperature varies depending upon the types of the starting materials and reagents used. However, it is usual to conduct the reaction within a range of from 0° to 50° C., preferably from 10° to 30° C.

The selective reduction of the thiocarbonate compound thus obtained, is preferably conducted by using alkyltin hydride in the presence of a radical initiator, followed by treatment with sodium alkoxide in an alcohol. As the radical initiator, bis-t-butylperoxide, bis-t-amylperoxide or tetrakis(triphenylphosphine)palladium may be mentioned. Particularly preferred is bis-t-butylperoxide. As the alkyltin hydride, trimethyltin hydride, triethyltin hydride, tri-n-propyltin hydride, tri-n-butyltin hydride, triphenyltin hydride or di-n-butyltin dihydride may be mentioned. Particularly preferred is tri-n-butyltin hydride. An aromatic compound such as benzene, toluene or xylene may be employed as the solvent for the reaction. However, it is preferred to use the alkyltin hydride itself as the solvent.

In order to hydrolyze the tin alcolate remaining as the result of the reaction with tin hydride, the treatment with sodium alkoxide is conducted in THF. As the sodium alkoxide, an alkoxide obtained by the usual method from methanol, ethanol or iso-propanol is preferred. Such a sodium alkoxide is used in an amount of at least 10 equivalents relative to the substrate. The reaction is conducted at a temperature of from 0° to 30° C.

Among the compounds of the formula I thus obtained, those having a double bond at the 5- or 6-position can be converted to 6-F-PGE$_1$ or 6-F-PGF$_1$ by selectively reducing the double bond, and if necessary, converting the 9-position to a carbonyl group or a hydroxymethylene group and optionally conducting the removal of a protecting group, the hydrolysis or the formation of a salt.

(C): Further, the compound of the formula I can be prepared by fluorinating a 6-hydroxy-PGF$_1$ of the formula VII, and optionally removing the protective group at the 9-position and conducting the oxidation of a hydroxyl group, the removal of a protecting group, the hydrolysis or the formation of a salt, as the case requires. There is no particular restriction as to the manner for the preparation of the compound of the formula VII. However, the compound of the formula VII can be prepared, for example, by using a basicaly known 6-keto-PGF$_1$ of the formula VIII as the starting material, and reducing the 6-carbonyl group of the starting material after protecting the hydroxyl group at the 9-position.

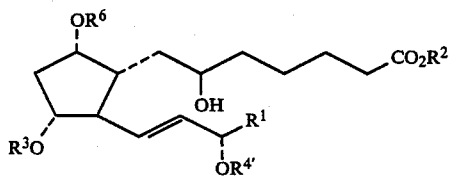
(VII)

wherein $R^1$, $R^2$, $R^3$ and $R^4$ are as defined above with respect to the formula I, and $R^6$ is a hydrogen atom or a protecting group. Further, during the fluorination reaction, it is usually required that $R^2$, $R^3$, $R^4$ are $R^{2'}$, $R^{3'}$ and $R^{4'}$, respectively, and $R^6$ is a protecting group $R^{6'}$.

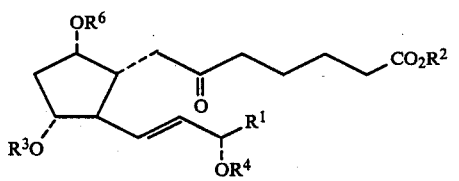
(VIII)

wherein $R^1$, $R^2$, $R^3$, $R^4$ and $R^6$ are as defind above with respect to the formula VII.

As the protecting group for the hydroxyl group at the 9-position, various protecting groups may be employed For example, it may be an acyl group, silyl group having three alkyl, aryl or aralkyl groups, a tetrahydropyranyl group, a tetrahydrofuranyl group, a benzyl group which may have a substituent or a methoxyethoxy group. Among such protecting groups, an acyl group such as an acetyl or benzoyl group which may have a substituent is mentioned as a preferred protecting group which is stable under the reducing and fluorinating conditions at the 6-position and which is effective for the improvement of the selectivity of the reaction. Particularly preferred is an acetyl group.

The acylation of the hydroxyl group at the 9-position may be conducted by a usual method. As the acylating agent, an acid anhydride such as an acetic anhydride or benzoic anhydride or an acid chloride such as acetyl chloride, benzoyl chloride or p-nitrobenzoyl chloride, may be used. As the base, an organic amine such as pyridine or triethylamine may be used. Here, it is preferred to add a catalytic amount of 4-dimethylaminopyridine to facilitate the reaction. The base itself may be used as a solvent. However, a halogenated hydrocarbon such as methylene chloride, chloroform or carbon tetrachloride, a hydrocarbon such as benzene or toluene, or an ether such as tetrahydrofuran or various alkyl ethers, or other solvents may be used.

The reduction of the carbonyl group at the 6-position is preferably conducted by means of a boron hydride compound such as sodium boron hydride, potassium boron hydride, lithium boron hydride or zinc boron hydride, or an aluminum hydride compound such as a diisobutylaluminum hydride-2,6-di-t-butyl-4-methylphenol system or an lithium aluminum hydride-binaphthol-ethanol system. Particularly preferred is the reduction by means of sodium boron hydride, a diisobutylaluminum hydride-2,6-di-6-butyl-4-methylphenol system or an lithium aluminum hydride-binaphthol-ethanol system.

As the solvent for the reaction in the case where the boron hydride compound is used, an alcohol such as methanol, ethanol or isopropanol is preferred. The reaction is usually conducted under cooling with ice. When the diisobutylaluminum hydride-2,6-di-t-butyl-4-methylphenol system is used, toluene or the like is preferred as the reaction solvent, and the reaction is usually conducted under cooling to $-78°$ C. for a few hours. In the case of the reduction by means of the aluminum lithium hydride-binaphthol-ethanol system, an ether solvent such as tetrahydrofuran is preferred.

The hydroxyl group at the 6-position of the compound of the formula VII thus obtained, is then fluorinated. This fluorination is conducted usually by adding a fluorinating agent to an alcohol or its derivative dissolved in a solvent.

For the fluorination of an alcohol, an aminosulfur fluoride type fluorinating agent such as

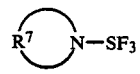

(wherein $R^7$ is a hydrocarbon forming a $C_4$–$C_7$ ring which may have oxygen) or

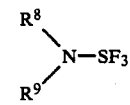

(wherein each of $R^8$ and $R^9$ which may be the same or different is a $C_1$–$C_5$ alkyl group), a polyfluoroolefin-dialkylamine type fluorinating agent (such as $CF_3CHFCF_2NEt_2$ or $CHClFCF_2NEt_2$), $SF_4$, $SeF_4$, $PhSF_3$, $PhPF_4$ or $Ph_3PF_2$, may be used as the fluorinating agent. A preferred fluorinating agent is an aminosulfur fluoride type fluorinating agent such as piperidinosulfur trifluoride, morpholinosulfur trifluoride or diethylaminosulfur trifluoride. When the aminosulfur fluoride type agent is used as the fluorinating agent, it is preferred to use a base together. For example, pyridine, triethylamine or N,N-dimethylaniline may be used as the base. As the solvent, a halogenated hydrocarbon such as methylene chloride, chloroform, carbon tetrachloride, fluorotrichloromethane or 1,1,2-trichlorotrifluoroethane, a hydrocarbon such as benzene or toluene, an ether such as tetrahydrofuran or various alkyl ethers, or other solvents, may be used. For the improvement of the selectivity of the fluorination, a halogenated hydrocarbon, particularly methylene chloride or carbon tetrachloride, is preferred. The reaction temperature is usually within a range of from $-100°$ to $25°$ C.

Further, it is possible to employ a fluorinating method wherein an alcohol is converted to a trimethylsilyl ether derivative, and then the above-mentioned aminosulfur fluoride type fluorinating agent is reacted (Japanese Unexamined Patent Publication No. 227888/1984).

Otherwise, it is possible to react the hydroxyl group at the 6-position with a reactive derivative of organosulfonic acid such as methanesulfonyl chloride, p-toluenesulfonyl chloride or trifluoromethanesulfonic acid anhydride in the presence of a basic compound such as pyridine or triethylamine to obtain a 6-organosulfonyloxy compound, which is then fluorinated with a fluorinating agent such as a metal fluoride or quaternary ammonium fluoride.

The removal of the protecting group at the 9-position can be conducted in an aqueous solution of e.g. sodium hydroxide, potassium hydroxide or calcium hydroxide, or in a water-alcohol mixture, in a methanol or ethanol solution containing sodium methoxide, potassium methoxide or sodium ethoxide.

The compounds obtained by the above methods (A) to (C) may optionally be further treated by the following methods for reducing the carbonyl group at the 9-position, or for selectively reducing the double bond in the α-chain, and, if necessary, for introducing a double bond at the 2- or 3-position or for conducting the removal of a protecting group, the hydrolysis or the formation of a salt.

Here, as a reducing agent useful for the selective reduction of the α-chain, a Lindlar catalyst, a palladium-barium sulfate-basic catalyst, a palladium-barium sulfate-synthetic quinoline catalyst, a palladium-carbon catalyst or an iridium-carbon catalyst may be mentioned. Particularly preferred is a palladium-barium slufate-basic catalyst or an iridium-carbon catalyst. To increase the selectivity in the reduction, a PGF derivative is particularly preferred as the base material, and a palladium-barium sulfate-basic catalyst or an iridium-carbon catalyst is preferred as the catalyst. The catalyst is used in an amount of from 0.1 to 10 parts by weight, preferably 1 part by weight, relative to 1 part of the base material. As the base used for the palladium-barium slufate-basic catalyst, triethylamine, pyridine or 2,6-dimethylpyridine may be mentioned. Particularly preferred is triethylamine. The base is used in an amount of from 1 to 50 equivalent, preferably from 10 to 20 equivalent, relative to the base material.

As the solvent, a hydrocarbon compound such as benzene, hexane or cyclohexane, an alcohol compound such as methanol, ethanol or isopropanol, or an ether compound such as THF, ethyl ether or dioxane, may be employed. Such a solvent is suitably selected depending upon the catalyst used. For example, in the case of a palladium-barium sulfate-triethylamine type catalyst, it is preferred to use THF for the improvement of the selectivity. The reaction is preferably conducted under a hydrogen pressure of from 1 to 5 atm, more preferably 1 atm.

The reaction temperature varies depending upon the types of the starting materials and the catalyst. However, the reaction is usually conducted within a range of from $-20°$ to $50°$ C., preferably from $0°$ to $30°$ C.

The reduction of the carbonyl group at the 9-position is preferably conducted by means of a boron hydride compound such as sodium boron hydride, potassium boron hydride, lithium boron hydride, lithium tri-s-butyl boron hydride or zinc boron hydride, or an aluminum hydride compound such as a diisobutylaluminum hydride-2,6-di-t-butyl-4-methylphenol system or an lithium aluminum hydride-binaphthol-ethanol system. Particularly preferred is the reduction by means of sodium boron hydride, a lithium tri-s-butylboron hydride, a diisobutylaluminum hydride-2,6-di-t-butyl-4-methylphenol system or an lithium aluminum hydride-binaphthol-ethanol system.

As the reaction solvent in the case where the boron hydride compound is used, an alcohol such as methanol, ethanol or isopropanol, or an ether such as THF, is preferred. The reaction is usually conducted at a temperature of from $-95°$ to $0°$ C. In the case where the diisobutylaluminum hydride-2,6-di-t-butyl-4-methylphenol system is used, the reaction solvent is preferably toluene or the like, and the reaction is conducted usually under cooling to $-78°$ C. for a few hours. In the case of the reduction by means of the aluminumlithium hydride-binaphthol-ethanol system, an ether solvent such as tetrahydrofuran is preferred.

On the other hand, various known methods may be employed for the oxidation of the hydroxyl group at the 9-position. Particularly preferred is a Corey-Kim oxidation method using N-chlorosuccinimidedimethylsulfide ("J. Org. Chem.", vol. 38, 1233 (1973)), a Jones oxidation method using chromium trioxide-sulfuric acid ("J. Chem. Soc.", vol. 38, (1946)) or a Collins oxidation method using chromium trioxide-pyridine ("Tetrahedron Lett.", 3363 (1968)). By the application of the reaction conditions as disclosed in the respective literatures, it is possible to obtain 6-F-PGE derivatives.

The introduction of a double bond at the 2- or 3-position can be conducted by applying a known method ("J. Am. Chem. Soc.", vol. 95, 6139 (1973)). Namely, a strong base such as lithium diisopropylamide is reacted to a PGF derivative (a compound of the formula I wherein A is a hydroxymethylene group) to generate the lithium enolate, then a phenylselenenyl group or a pyridinoselenenyl group is introduced thereto, and then this organic seleno group is oxidatively removed to obtain the desired compound.

After completion of the reaction, the product can be separated and purified by treating the reaction solution by usual methods. Namely, the separation and purification may be conducted by a proper combination of extraction, washing, drying, concentration, chromatography, etc. The product thus obtained, may further be subjected, if necessary, to the removal of the protecting group for the hydroxyl group at the 11- or 15-position. Or, the ester group at the 1-position may be hydrolyzed.

The removal of the protecting group for the hydroxyl group can be conducted as follows. When the protecting group is a group forming an acetal bond together with the oxygen atom of the hydroxyl group, the removal can efficiently be conducted by using e.g. acetic acid, a pyridinium salt of p-toluenesulfonic acid or cation exchange resin as the catalyst and e.g. water, tetrahydrofuran, ethyl ether, dioxane, acetone or acetonitrile as the reaction solvent. The reaction is conducted usually at a temperature within a range of from $-20°$ to $80°$ C. for from 10 minutes to three days. When the protecting group is a silyl group having three alkyl, aryl or aralkyl groups, the removal can be conducted at a substantially the same temperature for substantially the same period of time in the above-mentioned reaction solvent (preferably the reaction solvent other than water) in the presence of e.g. tetrabutylammonium fluoride or cesium fluoride (more preferably in the coexistence of a basic compound such as triethylamine). Otherwise, it is possible to employ a usual reaction for the removal of a protecting group by using an acidic compound such as hydrofluoric acid or acetic acid. When the protecting group is an acyl group, the removal can be conducted in an aqueous solution of e.g. sodium hydroixde, potassium hydroxide or calcium hydroxide, or in a water-alcohol mixture, or in a methanol or ethanol solution containing sodium methoxide, potassium methoxide or sodium ethoxide.

The hydrolysis of the ester group at the 1-position can be conducted, for example, by using an enzyme such as lipase or esterase in water or in a solution containing water at a temperature within a range of from $-10°$ to $60°$ C. for from 10 minutes to 24 hours. In the case of a PGF derivative, it is also possible to react it in water or in a solution containing water at a temperature within a range of from $-10°$ to $60°$ C. for from 10 minutes to 20 hours.

Among the compounds of the formula I of the present invention, those wherein both $R^3$ and $R^4$ are hydrogen atoms, i.e. the compounds of the formula I', are useful as drugs. Further, when $R^2$ is a hydrogen atom in the formula I', the compound may be in the form of a salt of such a carboxylic acid. Such a salt is a pharmaceutically acceptable non-toxic salt and can be obtained by neutralization with a basic substance in a theoretically equivalent amount. Specifically, an alkali metal salt or a non-toxic amine salt may be mentioned. As the basic substance, an alkali metal hydroxide such as sodium hydroxide or potassium hydroxide, an alkali metal carbonate such as sodium carbonate, ammonium hydroxide, ammonia or an amine such as triethylamine or monoethanol amine, may be mentioned.

The compound of the formula I' of the present invention and its salt have strong antiplatelet and antianginal effects and thus useful for the prevention or curing of thrombosis, anginapectoris, myocardial infarction or arteriosclerosis. Further, they have an inhibitory effect against gastric ulcer and thus is useful for the prevention and curing of gastric ulcer. The compound of the formula I' may be used as a drug even when $R^2$ is an alkyl group. However, as a drug, a compound of the formula I' wherein $R^2$ is a hydrogen atom is preferred. The 8-position usually takes S-configuration, but the phamacological effects are likewise observed when the 8-position takes R-configuration. Particularly preferred as a drug is a compound of the formula I' wherein A is a carbonyl group.

The phamacological test results of the compounds of the present invention are shown below.

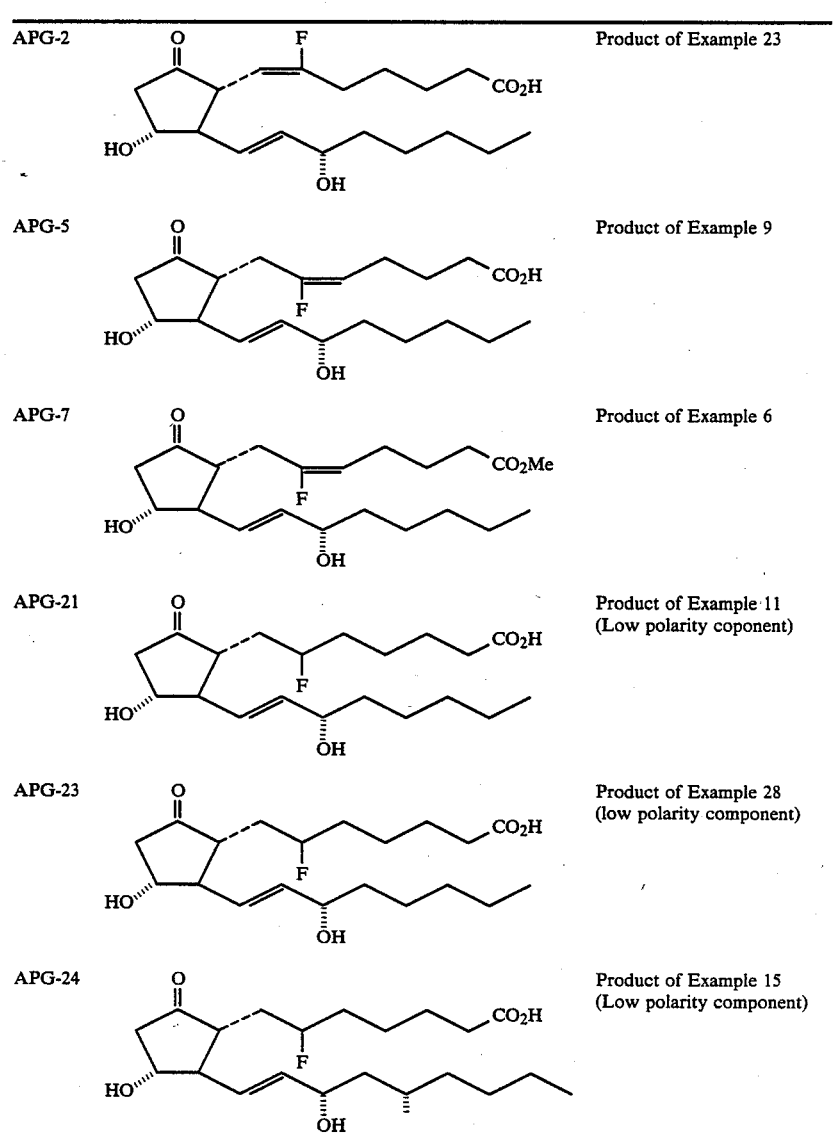

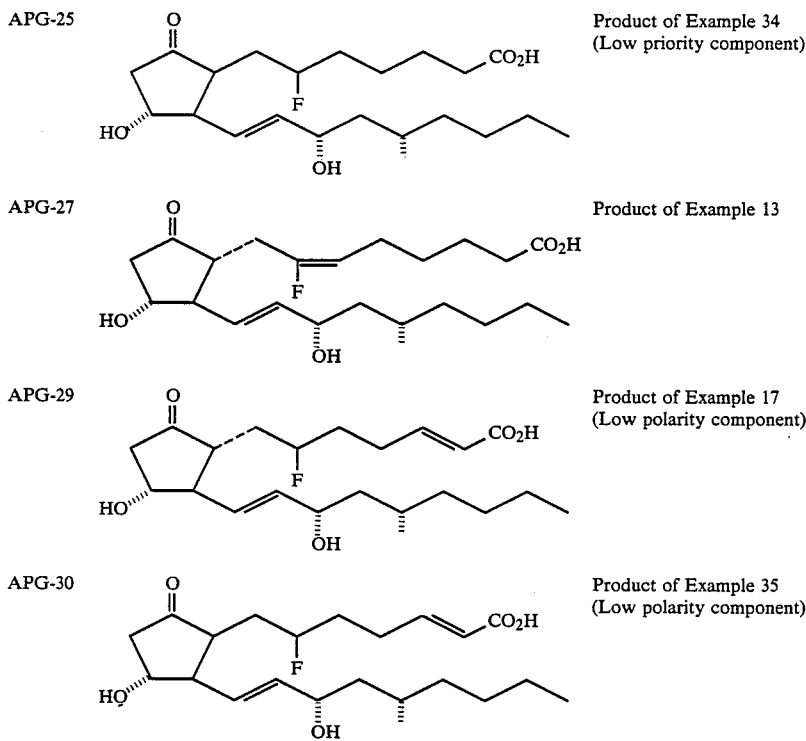

PHARMACOLOGICAL ACTIONS

Test Compounds:

Test compounds were dissolved in ethanol and diluted with 0.9% NaCl solution or 0.5% tragacanth solution.

Antiplatelet effect

Platelet aggregation study was carried out by a tarbidimetric method of Born (G. V. R. Born; Nature, 194, 927, 1962) using an aggregometer. Citrated blood obtained from guinea-pigs of Hartley strain was centrifuged at 120 g for 10 minutes and the supernatant, Platelet-rich plasma (PRP), was separated. In in vitro experiments, PRP was preincubated with test compounds at 37° C. for 10 minutes and then aggregation was induced by adding ADP (1 μM). Extent of aggregation was estimated with maximum changes of light transmittance within 5 minutes after adding ADP. Inhibitory potencies of compounds were expressed with the concentration showing 50% inhibition of platelet aggregation ($IC_{50}$). In ex vivo experiments, compounds were orally given to guinea-pigs. Blood was taken 5 hours after the administration of compounds, and platelet aggregation study was performed as described in in vitro experiments. Potencies of compnds was expressed with minimum dose showing significant inhibition (MED).

As shown in Table 1, the compounds of the present invention exhibited potent inhibitory effect on platelet aggregation in in vitro and even in ex vivo system, indicating that the compounds are considerably stable in in vivo. Thus, the compounds may be useful as medical agents.

ANTIANGINAL EFFECT

Antianginal effect of compounds was evaluated in male rats of Donryu strain according to Hatano et al. (N. Hatano et al.; Pharmacometrics, 19, 311, 1980) Vasopressin (0.2 IU/kg) was injected into femoral vein of anesthetized rats, and the depression in amplitude of ST-segment on ECG was measured at 30 second-intervals for 5 minutes after the vasopressin injection. Test compounds were intravenously injected 2 minutes before or orally given 30 minutes before the vasopressin injection. Data were analysed with two dimension analysis between the control and treated groups, and potencies of the compounds were expressed by MED. As shown in Table 2, the compounds of the present invention exhibited the potent antianginal effect.

INHIBITORY EFFECT ON GASTRIC ULCER

Gastric ulcer was induced by an oral administration of 0.4N HCl-50% ethanol (1 ml) to over night-fasted rats (male, Wister strain). One hour after HCl-ethanol administration, rats were sacrificed and their stomachs were isolated. Isolated stomachs were inflated with saline and fixed with 5% formalin. After fixation, the stomach was cut open along greater curvature and maximum length of each lesion was measured. The sum of lesion length was defined as the lesion index. Compounds were given orally 30 minutes before administration of HCl-ethanol. Potencies of compounds were expressed with $ED_{50}$, the dose required for 50% inhibition of lesion index.

As shown in Table 3, the compounds of the present invention possessed potent antiulcerogenic effect.

TABLE 1

| Compound | In Vitro $IC_{50}$ (ng/ml) ADP 1 μM | Ex vivo MED (mg/kg) |
|---|---|---|
| APG - 2 | 520 | — |
| APG - 5 | 490 | — |
| APG - 7 | 655 | — |

TABLE 1-continued

| Compound | In Vitro IC$_{50}$ (ng/ml) ADP 1 μM | Ex vivo MED (mg/kg) |
|---|---|---|
| APG - 21 | 100 | — |
| APG - 23 | 14.5 | — |
| APG - 24 | 5.9 | 0.3 |
| APG - 25 | 12.7 | 3.0 |
| APG - 27 | 42.7 | — |
| APG - 29 | 2.33 | 0.1 |
| APG - 30 | 1.05 | 1.0 |

TABLE 2

| Compound | I.V. MED (μg/kg) | P.O. MED (μg/kg) |
|---|---|---|
| APG - 24 | 10 | 0.1 |
| APG - 25 | 1.0 | 0.1 |
| APG - 29 | — | 0.1 |

TABLE 3

| Compound | ED$_{50}$ (μg/kg) |
|---|---|
| APG - 27 | 3.4 |
| APG - 29 | 1.8 |

The 6-fluoroprostaglandins of the present invention may be administered orally or non-orally such as subcutaneously, intramuscularly, intravenously, percutaneously or rectally. The drug formulations for oral administration include solid formulations such as tablets, granules, powders or capsules and liquid formulations such as emulsions, solutions, suspensions, syrups or elixirs. The tablets may be formed by a usual method by using an excipient such as lactose, starch, crystalline cellulose or polyvinylpyrrolidone, a binder such as carboxymethyl cellulose or methyl cellulose, or a disintegrator such as sodium arginate, sodiumhydrogen carbonate or sodiumlauryl carbonate. The granules and powders may also be formed by a usual method by using the above-mentioned excipient, etc. The capsules may be obtained by filling gelatine soft capsules with a solution prepared by dissolving the 6-fluoroprostaglandin of the present invention in a vegetable oil such as coconut oil.

The drug formulations for non-oral administration may be stabilized aqueous or non-aqueous solutions, suspensions or emulsions, or steril solid formulations which will be dissolved immediately prior to the use in a stabilized solvent for injection. Further, the drug formulations include suppository for rectal administration and pessaries for administration in vagina.

The 6-fluoroprostaglandins of the present invention may be used for drug formulation in the form of clathrate compounds with α-, β- or γ-cyclodextrine or methylated cyclodextrine.

The daily dose of the compound of the present invention is usually from 0.0001 to 1.0 mg/kg. In the intramuscular, subctaneous or intravenous administration, the dose is preferably within a range of from 0.0001 to 0.3 mg/kg. In the case of oral administration, the dose is preferably within a range of from 0.0001 to 1.0 mg/kg. However, the dose is not limited to such specific ranges, since it varies depending upon the age, the body weight and the degree of disease of the patient, the type of the disease and the number of times for administration.

Now, the present invention will be described in further detail with reference to Examples and Formulation Examples. However, it should be understood that the present invention is by no means restricted to such specific Examples.

PROCESS (A)

1. 2-fluoro-6-methoxycarbonyl-2-hexenyl iodide (a compound of the formula III wherein R$^2$ is a methyl group)

n-Butyl lithium (a hexane solution with f=1.69, 20.7 ml) was dissolved in THF (57 ml), and the solution was cooled to −78° C. To this solution, a solution of diethylcarboxyfluoromethane phosphonate (3.48 g, 16.3 mmol) in THF (25 ml) was dropwise added at −78° C. The mixture was stirred at the same temperature for 30 minutes. To this reaction solution, a solution of 4-methoxycarbonylbutanal (2.11 g, 16.3 mmol) in THF (16 ml) was dropwise added at −78° C., and the mixture was stirred at the same temperature. One hour later, the cooling bath was removed, and the mixture was stirred at room temperature for further one hour. Then, the reaction solution was cooled to 0° C., and water (40 ml) was added thereto. The mixture was vigorously stirred. The separated organic layer was extracted with a saturated sodium hydrogencarbonate aqueous solution (20 ml×2), and the extract solutions were combined with the previous aqueous layer, and the mixture was washed with ethyl ether (40 ml×2). The aqueous layer was adjusted to pH 4 by using hydrochloric acid under cooling with ice, and then sodium chloride was added to saturation. Then, the mixture was extracted with ethyl ether (40 ml×3), and the organic layer was dried over anhydrous magnesium sulfate. The solvent was distilled off under reduced pressure, and the residue was purified by silica gel column chromatography (methylene chloride/acetone=4/1 (containing 0.1% of acetic acid)) to obtain 2-fluoro-6-methoxycarbonyl-2-hexenoic acid (2.34 g, a mixture of E- and Z-isomers, yield: 76%) as yellow oil.

$^1$H-NMR (CDCl$_3$, TMC, mixture of E-isomer and Z-isomer): 6.25(1H, dt, J=30.8 Hz: Z-isomer), 6.04(1H, dt, J=20, 8 Hz: E-isomer), 3.69(3H, s).

$^{19}$F-NMR (CDCl$_3$, R-11): −130.7(d, J=30 Hz: Z-isomer), −121.6(d, J=20 Hz: E-isomer).

To this carboxylic acid (27.69 g, 145.6 mmol), oxalyl chloride (25.4 ml, 291.6 mmol) was added under cooling with ice, and the mixture was sitrred at 50° C. for 3 hours. The reaction solution was distilled under reduced pressure to obtain 2-fluoro-6-methoxycarbonyl-2-hexenoic acid chloride as colorless oil (26.07 g, yield: 86%).

Bp: 124°-134° C. (3.8 mmHg).

$^1$H-NMR (mixture of E-isomer and Z-isomer): 6.53 (1H, dt, J=30, 8 Hz), 6.11(1H, dt, J=15, 8Hz), 3.29(3H, s, COOCH$_3$).

$^{19}$F-NMR: −122.0 (d, J=30 Hz: Z-isomer), −113.2 (d, J=15 Hz: E-isomer).

This acid chloride (15.17 g, 72.7 mmol) wad dropwise added to a dioxane solution (290 ml) of sodium boron hydroxide (8.25 g, 218.2 mmol) under cooling with ice, and the mixture was stirred at room temperature for 30 minutes and further refluxed under heating for one hour. The reaction solution was cooled to 0° C., and a saturated ammonium chloride aqueous solution (200 ml) was added thereto, and the mixture was vigorously stirred. The organic solvent was distilled off under reduced pressure, and the remaining aqueous layer was extracted with ethyl ether (100 ml×3), and the organic layer was washed with a saturated sodium chloride aqueous solution (200 ml) and then dried over anhydrous magnesium sulfate. The solvent was distilled off under reduced pressure, and the residue thereby obtained was purified by silica gel column chromatography (hexane/ethyl acetate=3/1 to 2/1) to obtain 2-fluoro-6-methoxycarbonyl-2-hexenol as colorless oil (9.68 g, yield: 76%).

$^1$H=NMR (mixture of E-isomer and Z-isomer): 5.15 (1H, dt, $J_{HF}$=21.0 Hz: E-isomer), 4.83(1H, dt, $J_{HF}$=37.0 Hz: Z-isomer), 3.68(3H, s, —COOCH$_3$).

$^{19}$F-NMR: −120.3(dt, J=14.7, 37.0 Hz: Z-isomer), −112.2(dt, J=−21.0, 7.9 Hz: E-isomer).

Then, fluoro alcohol (2.23 g, 12.7 mmol) was dissolved in methylene chloride (63 ml), and triethylamine (2.66 ml, 19.1 mmol) was added thereto. The mixture was cooled to 0° C. To this solution, methanesulfonyl chloride (1.18 ml, 15.2 mmol) was dropwise added, and the mixture was stirred at room temperature for one hour. The reaction solution was poured into a saturated sodium hydrogencarbonate aqueous solution (60 ml) under cooling with ice. The mixture was vigorously stirred, and then the organic layer was separated. The aqueous layer was extracted with methylene chloride (20 ml×2), and the extract solutions were combined with the previous organic layer, and the mixture was washed with a saturated sodium chloride aqueous solution. The product was dried over anhydrous magnesium sulfate, and the solvent was distilled off under reduced pressure. The residue was dissolved in acetone (43 ml), and sodium iodide (2.86 g, 19.1 mmol) was added thereto. The mixture was refluxed for one hour. Acetone was removed under reduced pressure, and the residue was dissolved in ethyl ether (50 ml) and washed sequentially with water, a saturated sodium thiosulfate aqueous solution and a saturated sodium chloride aqueous solution. The organic layer was dried over anhydrous magnesium sulfate, and the solvent was removed under reduced pressure. The residue was purified by silica gel column chromatography (hexane/ethyl acetate=15/1) to obtain the desired iodide (3.28 g, yield: 90%) as slightly yellow oil.

$^1$H-NMR: 5.1(1H, dt, J=20, 7 Hz), 3.9 (1H, d, $J_{HF}$=−20 Hz), 3.7(3H, s.).

$^{19}$F-NMR: −104.4(dt, J=20, 20 Hz).

2. 6-fluoro-PGE$_2$ methyl ether 11,15-bis(t-butyldimethylsilyl ether) (a compound of the formula II wherein R$^1$ is a n-pentyl group, R$^2$ is a pentyl group, and each of R$^3$ and R$^4$ is a t-butyldimethylsilyl group)

An ethyl ether solution (2 ml) of (1E,3S)-1-iodo-3-(t-butyldimethylcyloxy)-1-octene (200 mg, 0.51 mmol) was cooled to −78° C., and t-butyl lithium (a pentane solution with f=1.80, 0.58 ml, 1.04 mmol) was dropwise added thereto. The mixture was stirred for two hours. Separately, tributylphosphine (0.33 ml, 1.33 mmol) and THF (2 ml) were added to cuprous iodide (97 mg, 0.51 mmol) to obtain a solution. This solution was dropwise added to the previous reaction solution at −78° C. by means of a stainless steel tube under an argon pressure while cooling the system to −78° C. The mixture was stirred under the same conditions for 10 minutes. Then, a THF solution (4 mg) of (R-4-(t-butyldimethylsiloxy)-2-cyclopentenone (106 mg, 0.50 mmol) was dropwise added thereto, and the mixture was stirred at −78° C. for one hour. Then, hexamethylphosphoric triamide (0.96 ml, 5.50 mmol) was dropwise added thereto at −78° C., and the mixture was stirred at the same temperature for 30 minutes. Then, a THF solution (2 ml) of triphenyltin chloride (193 mg, 0.50 mmol) was dropwise added at −78° C., and the mixture was stirred at the same temperature for 10 minutes. Finally, an ethyl ether solution (10 mmol) of the E-form iodide (715 mg, 2.50 mmol) obtained in the above Example 1, was dropwise added, and the reaction temperature was gradually raised to −20° C. The mixture was stirred for 16 hours. The reaction solution was diluted with ethyl ether, and the organic layer was washed sequentially with a saturated ammonium chloride aqueous solution and with a saturated sodium chloride aqueous solution. The product was dried and concentrated, and the residue was purified by silica gel column chromatography (hexane/ethyl acetate=15/1) at 0° C. to obtain the desired compound as yellow liquid (104 mg, yield: 32%).

$^1$H-NMR: 5.05(1H, dt, J=22, 8 Hz), 3.66(3H, s).

$^{19}$F-NMR: −102.8(dt, J=22, 14 Hz).

3. 6-fluoro-PGF$_2$α methyl ester 11,15-bis(t-butyldimethylsilyl ether) (a compound of the formula I wherein A is a hydroxymethylene group, R$^1$ is a n-pentyl group, R$^2$ is a methyl group, each of R$^3$ and R$^4$ is a t-butyldimethylsilyl group, R$^5$ is a hydrogen atom, and the 5-position is a double bond)

Diisobutylaluminium hydride (a 1M hexane solution, 8.2 ml, 8.2 mmol) was added at 0° C. to a toluene solution (8 ml) of 2,6-di-t-butyl-p-cresol (2.70 g, 12.3 mmol), and the mixture was stirred for one hour. This solution was dropwise added at −78° C. to a toluene solution (5 ml) of the 6-fluoro-PGE$_2$ derivative (500 mg, 0.82 mmol) obtained in Example 2. The mixture was stirred at −78° C. for two hours and at a temperature of from −40° to −20° C. for one hour. Then, a 1N hydrochloric acid aqueous solution (20 ml) was added to the reaction solution, and the mixture was returned to room temperature under vigorous stirring. The organic layer was separated, and the aqueous layer was extracted with ethyl acetate (10 ml×2). The extract solutions were combined with the previous organic layer, and the mixture was washed with a saturated sodium chloride aqueous solution (21 ml). The mixture was dried over anhydrous magnesium sulfate, and then the solvent was distilled off under reduced pressure. Then residue was purified at 0° C. by silica gel column chromatography (hexane/ethyl acetate=5/1) to obtain the above identified compound as colorless oil (48.2 mg, yield: 80%).

$^1$H-NMR: 4.97(1H, dt, J=22, 10 Hz).

$^{19}$F-NMR: −98.4(dt, J=22 Hz).

4. 6-fluoro-PGF$_1$α methyl ether 11,15-bis-(t-butyldimethylsilyl ether) (a compound of the formula I wherein A is a hydroxymethylene group, R$^1$ is a n-pentyl group, R$^2$ is a methyl group, each of R$^3$ and R$^4$ is a t-butyldimethylsilyl group, and R$^5$ is a hydrogen atom)

To a THF solution (3 ml) of the PGF$_2$ derivative (122 mg, 0.20 mmol) obtained in the preceding Example, triethylamine (0.3 ml) and a 5% palladium-barium sulfate catalyst (122 mg) were added. The mixture was stirred at room temperature for 3 hours under a hydrogen gas atmosphere. The solid in the reaction solution was separated by filtration, and the filtrate was concentrated under reduced pressure. The residue was purified at 0° C. by silica gel column chromatography (hexane/ethyl acetate=20/1) to obtain two types of 6-fluoro-PGF$_1$α derivatives (low polarity substance: 55 mg, yield: 45%, high polarity substance: 43 mg, yield: 35%) which appeared to be isomers at the 6-position.

Low polarity component:

$^1$H-NMR: 4.72(1H, dm, $J_{HF}$=51 Hz), 3.66(3H, s)

$^{19}$F-NMR: −180.4(m).

High polarity component:

$^1$H-NMR: 4.62(1H, dm, $J_{HF}$=49 Hz), 3.66(3H, s)

19F-NMR: −180.7(m).

5. 6-fluoro-PGE$_1$ methyl ester 11,15 (t-butyldimethylsilyl ether) (a compound of the formula I wherein A is a carbonyl group, R$^1$ is a n-pentyl group, R$^2$ is a methyl group, each of R$^3$ and R$^4$ is a t-butyldimethylsilyl group, and R$^5$ is hydrogen atom)

Dimethyl sulfide (57 ml, 0.76 mmol) was dropwise added at 0° C. to a toluene solution (2.6 ml) of N-chlorosuccinimide (85 mg, 0.64 mmol). This solution was cooled to −25° C., and then a toluene solution (0.65 ml) of the low polarity isomer of 6-fluoro-PGF$_{1α}$ derivative (87.6 mg, 0.14 mmol) obtained in the preceding Example, was dropwise added thereto. The mixture was stirred at −25° C. for two hours, and then a n-pentane solution (0.26 ml) of triethylamine (175 ml, 1.26 mmol) was added thereto. The organic layer was washed with a 1% hydrochloric acid aqueous solution (2 ml) cooled with ice and then further washed with ice water (3 ml×2). The organic layer was dried over anhydrous magnesium sulfate, and then the solvent was distilled off under reduced pressure. The residue thereby obtained was purified at 0° C. by silica gel column chromatography (hexane/ethyl acetate=7/1) to obtain a PGE$_1$ derivative as colorless oil (82.5 mg, yield: 96%).

$^1$H-NMR: 4.45(1H, dm, J=50 Hz).
$^{19}$F-NMR: −185.7(m).

The high polarity isomer was oxidized in the same manner to obtain a corresponding PGE$_1$ derivative as colorless oil (82.5 mg, yield: 96%).

$^1$H-NMR: 4.40(1H, dm, J=50 Hz).
$^{19}$F-NMR: −187.0(m).

6. 6-fluoro-PGE$_2$ methyl ester (a compound of the formula I, wherein A is a carbonyl group, R$^1$ is a n-pentyl group, R$^2$ is a methyl group, each of R$^3$, R$^4$ and R$^5$ is a hydrogen atom, and the 5-position is a double bond)

A 40% hydrogen fluoride aqueous solution (1.1 ml) was added at 0° C. to an acetonitrile solution (7.0 ml) of the 6-fluoro-PGE$_2$ methyl ester 11,15-bis(t-butyldimethylsilyl ether) (200 mg, 0.33 mmol) obtained in Example 2, and the mixture was stirred at room temperature for one hour. To the reaction solution, ice water (25 ml) was added, and the mixture was extracted with chloroform (10 ml×7). The organic layers were put together, and the mixture was dried over anhydrous magnesium sulfate. Then, the solvent was distilled off under reduced pressure. The residue was purified at 0° C. by silica gel column chromatography (methylene chloride/acetone=5/2) to obtain the above identified compound as colorless oil (102 mg, yield: 82%).

$^1$H-NMR: 5.04(1H, dt, J=22, 8 Hz).
$^{19}$F-NMR: −102.1(dt, J=22 Hz).

7. 6-fluoro-PGF$_{2α}$ methyl ester (a compound of the formula I wherein A is a hydroxymethylene group, R$^1$ is a n-pentyl group, R$^2$ is a methyl group, each of R$^3$, R$^4$ and R$^5$ is a hydrogen atom, and the 5-position is a double bond)

The 6-fluoro-PGF$_2$ methyl ester 11,15-bis(t-butyldimethylsilyl ether) obtained in Example 3 was treated in the same manner as in the preceding Example to obtain the above identified compound.

$^1$H-NMR: 4.56(1H, dt, J$_{HF}$=21 Hz, J=8 Hz), 3.66(3H, s).
$^{19}$F-NMR: −109.6(dt, J=21, 14 Hz).

8. 6-fluoro-PGE$_1$ methyl ester (a compound of the formula I wherein A is a carbonyl group, R$^1$ is a n-pentyl group, R$^2$ is a methyl group, and each of R$^3$, R$^4$ and R$^5$ is a hydrogen atom)

The low polarity component of the 6-fluoro-PGE$_1$ derivative obtained in Example 5 was treated in the same manner as in the preceding Example to obtain the above identified compound as colorless oil (yield: 83%).

$^1$H-NMR: 4.57(1H, dm, J$_{HF}$=49 Hz), 3.66(3H, s).
$^{19}$F-NMR: −183.4(m).

Likewise, from the high polarity isomer, the corresponding methyl ester was obtained in a yield of 78%.

$^1$H-NMR: 4.40(1H, dm, J$_{HF}$=50 Hz), 3.65(3H, s).
$^{19}$F-NMR: −184.7(m).

9. 6-fluoro-PGE$_2$ (a compound of the formula I wherein A is carbonyl group, R$^1$ is a n-pentyl group, each of R$^2$, R$^3$, R$^4$ and R$^5$ is a hydrogen atom, and the 5-position is a double bond)

To an acetone solution (0.55 ml) of the methyl ester (50 mg, 0.13 mmol) obtained in Example 6, a phosphate buffer (5.5 ml) of pH 8 was added, and a pig liver esterase aqueous solution (manufactured by Sigma Co., pH 8) (0.11 ml) was further added thereto. The mixture was stirred at room temperature for 4 hours. The reaction solution was cooled to 0° C. and adjusted to pH 4 with 1N hydrochloric acid. Then, ammonium sulfate was saturated. This solution was extracted with ethyl acetate (3 ml×10), and the organic layer was washed with a saturated sodium chloride aqueous solution (10 ml) and then dried over anhydrous magnesium sulfate. The solvent was distilled off under reduced pressure. The residue thereby obtained was purified by high performance liquid chromatography (column: YMCPAK-ODS, acetonitrile/water=4/6) containing 0.1% acetic acid)) to obtain carboxylic acid (40 mg, yield: 82%) as colorless oil.

$^1$H-NMR: 5.05(1H, dt, J=22, 8 Hz).
$^{19}$F-NMR: −102.3(dt, J=22, 14 Hz).

10. 6-fluoro-PGF$_{2α}$ (a compound of the formula I wherein A is a hydroxymethylene group, R$^1$ is a n-pentyl group, each of R$^2$, R$^3$, R$^4$ and R$^5$ is a hydrogen atom, and the 5-position is a double bond)

The methyl ester compound (10.9 mg, 0.028 mmol) obtained in Example 7 was dissolved in methanol (0.5 ml) and water (0.5 ml), and a 0.74N sodium hydroxide aqueous solution (0.2 ml) was added thereto under cooling with ice. The mixture was stirred at room temperature for 18 hours. The reaction solution was adjusted to pH 4 with 0.1N hydrochloric acid. Then, the reaction solution was saturated with sodium chloride and repeatedly extracted with ethyl acetate (1 ml×10). The extract was washed with a saturated sodium chloride aqueous solution. The organic layer was dried and concentrated under reduced pressure to obtain the above identified compound (10 mg, yield: 91%).

$^1$H-NMR: 4.56(1H, dt, J$_{HF}$=21 Hz, J=8 Hz).
$^{19}$F-NMR: −109.5(dt, J=21, 14 Hz).

11. 6-fluoro-PGE$_1$ (a compound of the formula I wherein A is a carbonyl group, R$^1$ is a n-pentyl group, and each of R$^2$, R$^3$, R$^4$ and R$^5$ is a hydrogen atom)

The compound obtained in Example 8 was hydrolyzed in the same manner as in Example 9 to obtain the desired compound as colorless oil (yield: 96%).

Low polarity component
$^1$H-NMR: 4.71(1H, dm, J$_{HF}$=49 Hz).
$^{19}$F-NMR: −180.6(m).
High polarity component
$^1$H-NMR: 4.70(1H, dm, J$_{HF}$=49 Hz).
$^{19}$F-NMR: −177.1(m).

12. (17S)-17,20-dimethyl-6-fluoro-PGE$_2$ methyl ester 11,15-bis(t-butyldimethylsilyl ether) (a compound of the formula II wherein R$^1$ is a (2S)-2-methylhexyl group, $R^2$ is a methyl group, each of $R^3$ and $R^4$ is a t-butyldimethylsilyl group)

The above identified compound was obtained in a yield of 72% by using (1E,3S,5S)-1-iodo-3-(t-butyldimethylsiloxy)-5-methyl-1-nonene instead of (1E,3S)-1-iodo-3-(t-butyldimethylsiloxy)-1-octene in Example 2.

$^1$H-NMR: 5.05(1H, dt, J=21, 8 Hz), 3.67(3H, s).
$^{19}$F-NMR: −102.8(dt, J=21, 14 Hz).

In the same manner as in the preceding Examples, the following 6-F-17,20-dimethyl-PG derivatives were prepared.

13. (17S)-17,20-dimethyl-6-fluoro-PGE$_2$ (a compound of the formula I wherein A is a carbonyl group, $R^1$ is a (2S)-2-methylhexyl group, each of $R^2$, $R^3$, $R^4$ and $R^5$ is a hydrogen atom, and the 5-position is a double bond)

$^1$H-NMR: 5.05(1H, dt, J=21, 8 Hz).
$^{19}$F-NMR: −102.3(dt, J=22, 14 Hz).

14. (17S)-17,20-dimethyl-6-fluoro-PGF$_{2\alpha}$ (a compound of the formula I wherein A is a hydroxymethylene group, $R^1$ is a (2S)-2-methylhexyl group, and each of $R^2$, $R^3$, $R^4$ and $R^5$ is a hydrogen atom)

$^1$H-NMR: 4.58(1H, dt, J=21, 8 Hz)
$^{19}$F-NMR: −109.5(dt, J=21, 14 Hz)

15. (17S)-17,20-dimethyl-6-fluoro-PGE$_1$ (a compound of the formula I wherein A is a carbonyl group, $R^1$ is a (2S)-2-methylhexyl group, and each of $R^2$, $R^3$, $R^4$ and $R^5$ is a hydrogen atom)

The product was a mixture of the 6-position epimers.

Low polarity component
$^1$H-NMR: 4.71(1H, dm, $J_{HF}$=47 Hz).
$^{19}$F-NMR: −180.5(m).

High polarity component
$^1$H-NMR: 4.70(1H, dm, $J_{HF}$=47 Hz).
$^{19}$F-NMR: −177.0(m).

16. Δ$^2$-(17S)-17,20-dimethyl-6-fluoro-PGF$_{1\alpha}$ methyl ester 11,15-bis(t-butyldimethylsilyl ether) (a compound of the formula I wherein A is a hydroxymethylene group, $R^1$ is a (2S)-2-methylhexyl group, $R^2$ is a methyl group, each of $R^3$ and $R^4$ is a t-butyldimethylsilyl group, $R^5$ is a hydrogen atom, and the 2-position is a double bond)

To a THF solution of diisopropylamine (0.06 ml, 0.413 mmol), n-butyl lithium (a 1.51M hexane solution, 0.274 ml, 0.413 mmol) was added at −70° C., and the mixture was stirred at the same temperature for 20 minutes. To this solution, a THF solution (0.47 ml) of the low polarity component of (17S)-17,20-dimethyl-6-fluoro-PGF$_1$ methyl ester 11,15-bis(t-butyldimethylsilyl ether) (101 mg, 0.157 mmol) was dropwise added at −70° C., and the mixture was stirred at the same temperature for 20 minutes. Then, a THF solution (0.47 ml) of diphenyldiselenide (103 mg, 0.157 mmol) was dropwise added thereto, and the mixture was stirred at −70° C. for 45 minutes and at 0° C. for one hour. To the reaction solution, a saturated ammonium chloride aqueous solution (5 ml) was added, and the organic layer was extracted with ethyl ether. The ether solution was washed with a saturated sodium chloride aqueous solution, then dried and concentrated. The residue was purified by silica gel column chromatography (hexane/ethyl acetate=7/1) to obtain 2-phenylseleno compound (92 mg, yield: 73%).

This 2-phenylseleno compound (92 mg, 0.115 mmol) was dissolved in a solution mixture of ethyl acetate (0.735 ml) and THF (0.367 ml), and sodium hydrogen carbonate (32 mg) was added thereto. A 30% hydrogen peroxide aqueous solution (0.039 ml) was dropwise added thereto at 35° C., and the mixture was stirred at the same temperature for 30 minutes. The reaction solution was diluted with ethyl acetate (5 ml) and washed with a saturated sodium hydrogen carbonate aqueous solution and with a saturated sodium chloride aqueous solution. The organic layer was dried and concentrated. The residue was purified by silica gel column chromatography (hexane/ethyl acetate=7/1) to obtain the above identified compound (69 mg, yield: 93%).

$^1$H-NMR: 4.58(1H, dm, $J_{HF}$=47 Hz), 5.83(1H, d, J=16 Hz), 6.93(1H, dt, J=16, 7 Hz).
$^{19}$F-NMR: −182.0(m).

The high polarity component of (17S)-17,20-dimethyl-6-fluoro-PGF$_{1\alpha}$ methyl ester 11,15-bis(t-butyldimethylsilyl ether) can also be converted to the Δ$^2$ derivative in the same manner.

17. Δ$^2$-(17S)-17,20-dimethyl-6-fluoro-PGE$_1$ (a compound of the formula I wherein A is a carbonyl group, $R^1$ is a (2S)-2-methylhexyl group, each of $R^2$, $R^3$, $R^4$ and $R^5$ is a hydrogen atom, and the 2-position is a double bond)

The methyl ester (69 mg, 0.108 mmol) obtained in Example 16 was hydrolyzed in the same manner as in Example 10 to convert it to a carboxylic acid (yield: 83%).

This carboxylic acid (56 mg, 0.089 mmol) was dissolved in ethyl ether (3 ml), and a chromic acid solution (4.4 ml) prepared in a usual manner, was added thereto at 0° C., and the mixture was stirred at the same temperature for two hours. The reaction solution was extracted with ethyl ether (5 ml×3), and the organic layer was washed with water and a saturated sodium chloride aqueous solution. The organic layer was dried and concentrated to obtain a colorless PGE$_1$ derivative (54 mg, yield: 97%).

To an acetonitrile solution (0.6 ml) of this silyl ether (54 mg, 0.086 mmol), a 40% hydrogen fluoride solution (0.45 ml) was added at 0° C., and the mixture was stirred at room temperature for one hour. To the reaction solution, ice water (10 ml) was added, and the mixture was extracted with chloroform. The organic layers were put together, dried and concentrated, and the residue was purified by high performance liquid chromatography (column: YMCPACK-ODS, acetonitrile/water=4/6 (containing 0.1% acetic acid)) to obtain the above identified compound as a colorless liquid (26 mg, yield: 73%).

$^1$H-NMR: 4.71(1H, dm, $J_{HF}$=47 Hz), 5.83(1H, d, J=16 Hz), 6.93(1H, dt, J=16, 7 Hz).
$^{19}$F-NMR: −182.0(m).

PROCESS B 18. 2-fluoro-6-methoxycarbonyl-2-hexenal (a compound of the formula VI wherein $R^2$ is a methyl group)

To a methylene chloride solution (74 ml) of oxalyl chloride (3.55 ml, 40.7 mmol), a methylene chloride solution (13.6 ml) of dimethylsulfoxide (6.22 ml, 87.6 mmol) was dropwise added at −60° C.

The mixture was stirred at −60° C. for 15 minutes, and a methylene chloride solution (27 ml) of 2-fluoro-6-methoxycarbonyl-2-hexenol (5.52 g, 31.3 mmol) as the intermediate of Example 1, was dropwise added thereto at the same temperature. The mixture was stirred for 40 minutes. Then, triethylamine (28.4 ml, 203.5 mmol) was added thereto at −60° C., and the mixture was stirred at the same temperature for 15 minutes and then at room temperature for 30 minutes. To the reaction solution, water (60 ml) was added, and the mixture was vigorously stirred. Then, the organic layer was separated. The aqueous layer was extracted with methylene chloride (30 ml×2), and the extracts were combined with the previous organic layer. This organic layer was washed with a saturated sodium chloride aqueous solution (100 ml) and then dried over anhydrous magenesium sulfate. The solvent was distilled off under reduced pressure, and the residue was purified by silica gel column chromatography (hexane/ethyl acetate=7/1) to obtain an E-form aldehyde (1.60 g, yield: 29%) and a Z-form isomer (1.80 g, yield: 33%) as colorless oils.

E-form aldehyde:

$^1$H-NMR: 9.74(1H, d, J=15 Hz), 6.16(1H, dt, J=18, 9 Hz), 3.69(3H, s).

$^{19}$F-NMR: −127.1(dd, J=15, 18 Hz).

Z-form aldehyde:

$^1$H-NMR: 9.23(1H, d, J=18 Hz), 5.95(1H, dt, J=32, 8 Hz), 3.69(3H, s).

$^{19}$F-NMR: −133.2(dd, J=20, 32 Hz).

19. 6-fluoro-7-hydroxy-PGE$_2$ methyl ester 11,15-bis(t-butyldimethylsilyl ether) (a compound of the formula IV wherein $R^1$ is a n-pentyl group, $R^2$ is a methyl group, and each of $R^3$ and $R^4$ is a t-butyldimethylsilyl group)

An ethyl ether solution (54 ml) of (1E,3S)-1-iodo-3-(t-butyldimethylsiloxy)-1-octene (4.93 g, 13.4 mmol) was cooled to −78° C., and t-butyl lithium (a hexane solution with f=1.80, 15.2 ml, 27.3 mmol) was dropwise added thereto. The mixture was stirred for two hours. Separately, 1-pentynecopper (1.75 g, 13.4 mmol) was dissolved in hexamethylphosphorous triamide (4.87 ml, 26.8 mmol), and then it was diluted with ethyl ether (54 ml) and cooled to −78° C. This solution was dropwise added to the previous reaction solution at −78° C. by means of a stainless steel tube under an argon pressure at −78° C. The mixture was stirred under the same condition for 30 minutes. Then, an ethyl ether solution (54 ml) of (R)-4-t-butyldimethylsiloxy)-2-cyclopentanone (2.80 g, 13.2 mmol) was dropwise added by means of a stainless steel tube under the same argon pressure as above. The mixture was stirred at −78° C. for 10 minutes and at −40° C. for 20 minutes. Then, an ethyl ether solution (54 ml) of (2E)-2-fluoro-6-methoxycarbonyl-2-hexenal (2.53 g, 14.5 mmol) previously cooled to −78° C., was dropwise added by means of a stainless steel tube under an argon pressure, and the mixture was stirred at −40° C. for one hour. The reaction solution was poured into a mixture of an acetic acid buffer solution (500 ml) of pH 4 and hexane (300 ml) at 0° C. under vigorous stirring, and then stirred for 15 minutes. Precipitated solid was filtered off, and the organic layer was separated. The organic layer was washed with a mixture of a saturated ammonium chloride agueous solution and aqueous ammonia solution (200 ml×3), with a saturated ammonium chloride aqueous solution (300 ml) and with a saturated sodium chloride aqueous solution (300 ml) sequentially and dried over anhydrous magnesium sulfate. The solvent was distilled off under reduced pressure, and the residue was purified by silica gel chromatography at 0° C. (hexane/ethyl acetate=6/1) to obtain the desired compound as yellow oil (5.00 g, yield: 60%).

$^1$H-NMR: 5.18(1H, dt, J=21, 8 Hz), 4.67(1H, ddd, J$_{HF}$=26 Hz, J=8, 3 Hz), 3.67(3H, s).

$^{19}$F-NMR: −120.5(dt, J=21, 26 Hz).

20. Δ$^7$-6-fluoro-PGE$_2$ methyl ester 11,15-bis(t-butyldimethylsilyl ether) (a compound of the formula V wherein $R^1$ is a n-pentyl group, $R^2$ is a methyl group, and each of $R^3$ and $R^4$ is a t-butyldimethylsilyl group)

The compound obtained in Example 19 (3.14 g, 5.0 mmol) was dissolved in methylene chloride (25 ml), and 4-dimethylaminopyridine (1.83 g, 45 mmol) and then methanesulfonyl chloride (0.58 ml, 7.5 mmol) were added thereto at 0° C. The mixture was stirred at room temperature for 15 hours, and then the reaction solution was poured into a saturated sodium hydrogen carbonate aqueous solution (850 ml) at 0° C. The mixture was vigorously stirred. The organic layer was separated. Then, the aqueous layer was extracted with ethyl ether (30 ml×2), and the extracts were combined to the previous organic layer. The mixture was washed with a saturated sodium chloride aqueous solution (50 ml). The organic layer was dried over anhydrous magnesium sulfate, and then the solvent was distilled off under reduced pressure. The residue was purified by silica gel column chromatography at 0° C. (hexane/ethyl acetate=8/1) to obtain a dienone compound as yellow oil (2.29 g, yield: 75%).

$^1$H-NMR: 5.50(1H, dd, J$_{HF}$=17 Hz, J=9 Hz), 4.27(1H, d, J$_{HF}$=4 Hz), 3.68(3H, s).

$^{19}$F-NMR: −113.4(dd, J=21, 35 Hz).

21. (6E)-Δ$^6$-6-fluoro-PGE$_1$ ethyl ester 11,15-bis(t-butyldimethylsilyl ether) (a compound of the formula I wherein A is a carbonyl group, $R^1$ is a n-pentyl group, $R^2$ is a methyl group, each of $R^3$ and $R^4$ is a t-butyldimethylsilyl group, $R^5$ is a hydrogen atom, and the 6-position is a E-form double bond)

The dienone compound obtained in Example 20 (500 mg, 0.82 mmol) was dissolved in isopropyl alcohol (12 ml). Then, zinc powder (1.07 g, 16.4 mmol) and acetic acid (2.43 ml) were added thereto. The mixture was stirred at 50° C. for 1.5 hours. The reaction solution was returned to room temperature and then diluted with ethyl acetate (50 ml). Solid was separated by filtration, and washed sequentially with water (30 ml), with a saturated sodium hydrogen carbonate aqueous solution (30 ml) and with a saturated sodium chloride aqueous solution (30 ml) and then dried over anhydrous magnesium sulfate. The solvent was distilled off under reduced pressure, and then the residue was purified by silica gel column chromatography at 0° C. (hexane/ethyl acetate=15/1) to obtain 6-fluoro-PGE$_2$ derivative (64 mg, yield: 13%), (6E)-Δ$^6$-fluoro-PGE$_1$ derivative (113 mg, yield: 23%) and (6E)-8-ent-Δ$^6$-6-fluoro-PGE$_1$ derivative (146 mg, yield: 29%) as colorless oils.

(6E)-Δ$^6$-6-fluoro-PGE$_1$ methyl ester 11,15-bis(t-butyldimethylsilyl ether)

$^1$H-NMR: 5.47–5.60(2H, m), 4.84(1H, dd, J$_{HF}$=21 Hz, J=10 Hz).

$^{19}$F-NMR: −98.7(dt, J=21, 8 Hz).

(6E)-8-ent-Δ$^6$-6-fluoro-PGE$_1$ methyl ester 11,15-bis(t-butyldimethylsilyl ether)

$^1$H-NMR: 5.08–5.62(2H, m), 4.79(1H, dd, J$_{HF}$=21 Hz, J=10 Hz).

$^{19}$F-NMR: −99.4(dt, J=21, 8 Hz)

22. (6Z)-Δ$^6$-6-fluoro-PGF$_1$ methyl ester 11,15-bis(t-butyldimethylsilyl ether) (a compound of the formula I wherein A is a hydroxymethylene group, $R^1$ is a n-pentyl group, $R^2$ is a methyl group, each of $R^3$ and $R^4$ is a t-butyldimethylsilyl group, $R^5$ is a hydrogen atom, and the 6-position is a Z-form double bond) and (6Z)-Δ$^6$-6-fluoro-PGF$_1$ 11,15-bis(t-butyldimethylsilyl ether) (a compound of the formula I wherein A is a hydroxymethylene group, $R^1$ is a n-pentyl group, $R^2$ is a hydrogen atom, each of $R^3$ and $R^4$ is a t-butyldimethylsilyl group, $R^5$ is a hydrogen atom, and the 6-position is a double bond)

To an absolute methanol solution (18 ml) of hydroxyketone (1.00 g, 1.59 mmol) obtained in Example 19, sodium borohydride (181 mg, 4.78 mmol) was added at once at $-10°$ C., and the mixture was stirred for 30 minutes at the same temperature. A saturated ammonium chloride aqueous solution (10 ml) was dropwise added thereto. Then, methanol is distilled off under reduced pressure. The residue was extracted with ethyl ether, and the ether layer was washed with a saturated sodium chloride aqueous solution, dried and concentrated. The product was purified by column chromatography (hexane/ethyl acetate=2/1) to obtain 758 mg (yield: 75%) of 7-hydroxy-6-fluoro-PGF$_1$ methyl ester 11,15-(t-butyldimethylsilyl ether).

To an acetonitrile solution (5 ml) of this diol (373 mg, 0.592 mmol), 1,1'-thiocarbonyldiimidazole (106 mg, 0.592 mmol) and 4-dimethylaminopyridine (72 mg, 0.592 mmol) were added, and the mixture was stirred at room temperature for 12 hours. Dilute hydrochloric acid cooled with ice and ethyl ether were added, and the ether layer was washed with water and with a saturated sodium chloride aqueous solution, dried and concentrated. The residue was purified by flash column chromatography (hexane/ethyl acetate=4/1) to obtain a thiocarbonate compound (312 mg, yield: 72%).

A mixture comprising this thiocarbonate compound (312 mg, 0.426 mmol), tri-n-butyltin hydride (3 ml) and bis-t-butyl peroxide (12 mg) was stirred at 55° C. for one hour. After cooling the mixture, a mixture comprising a methanol solution (3 ml) of 1N sodium methoxide and THF (3 ml) was added thereto, and the mixture was stirred at room temperature overnight. The mixture was neutralized with dilute hydrochloric acid cooled with ice, and then the solvent was removed under reduced pressure. To the residue, ethyl ether and a saturated sodium chloride aqueous solution were added, and the aqueous layer was repeatedly extracted with ethyl ether. The ether solutions were put together, washed with a saturated sodium chloride aqueous solution, dried and concentrated. The residue was purified by column chromatography (hexane/ethyl acetate=4/1→ethyl acetate) to obtain (6Z)-$\Delta^6$-6-fluoro-PGF$_1$ methyl ester derivative (94 mg, yield: 32%) and (6Z)-$\Delta^6$-6-fluoro-PGF$_1$ derivative having the methyl ester group hydrolyzed (104 mg, yield: 39%).

(6Z)-$\Delta^6$-6-fluoro-PGF$_1^\alpha$ methyl ester 11,15-bis(t-butyldimethylsilyl ether)

$^1$H-NMR: 4.72(1H, dd, $J_{HF}$=38 Hz, J=10 Hz).
$^{19}$F-NMR: $-107.0$(dt, J=38, 17 Hz).

(6Z)-$\Delta^6$-6-fluoro-PGF$_1$ 11,15-bis(t-butyldimethylsilyl ether)

$^1$H-NMR: 4.72(1H, dd, $J_{HF}$=38 Hz, J=10 Hz).
$^{19}$F-NMR: $-106.8$(dt, J=38, 18 Hz).

23. (6E)-$\Delta^6$-6-fluoro-PGE$_1$ (a compound of the formula I wherein A is a carbonyl group, $R^1$ is a n-pentyl group, each of $R^2$, $R^3$, $R^4$ and $R^5$ is a hydrogen atom, and the 6-position is an E-form double bond)

The product obtained in Example 21, was subjected to the removal of the silyl protecting group in the same manner as in Example 6 and then to the hydrolysis of the methyl ester in the same manner as in Example 9 to obtain the above identified compound.

$^1$H-NMR: 4.84(1H, dd, J=21, 10 Hz).
$^{19}$F-NMR: $-98.8$(dt, J=21, 8 Hz).

24. (6E)-8-ent-$\Delta^6$-6-fluoro-PGE$_1$ (a compound of the formula I wherein the 8-position is a R-form, A is a carbonyl group, $R^1$ is a n-pentyl group, each of $R^2$, $R^3$, $R^4$ and $R^5$ is a hydrogen atom, and the 6-position is an E-form double bond)

$^1$H-NMR: 5.25–5.75(2H, m), 4.79(1H, dd, $J_{HF}$=21 Hz, J=10 Hz).
$^{19}$F-NMR: $-99.4$(dt, J=21, 8 Hz).

25. (6Z)-$\Delta^6$-6-fluoro-PGF$_1$ (a compound of the formula I wherein A is a hydroxymethylene group, $R^1$ is a n-pentyl group, each of $R^2$, $R^3$, $R^4$ and $R^5$ is a hydrogen atom, and the 6-position is a Z-form double bond)

(6Z)-$\Delta^6$-6-fluoro-PGF$_1$ 11,15-bis(t-butyldimethylsilyl ether) obtained in Example 22 was treated with a 40% hydrogen fluoride aqueous solution in the same manner as in the preceding Examples, and the product was purified by high performance liquid chromatography (column: YMCPACK-ODS, acetonitrile/water=4/6) containing 0.1% acetic acid) to obtain the above identified compound.

$^1$H-NMR: 4.72(1H, dd, $J_{HF}$=38 Hz, J=10 Hz).
$^{19}$F-NMR: $-107.1$(dt, J=38, 17 Hz).

26. (6E)-8-ent-$\Delta^6$-6-fluoro-PGF$_1$ (a compound of the formula I wherein the 8-position is a R-form, A is a hydroxymethylene group, $R^1$ is a n-pentyl group, each of $R^2$, $R^3$, $R^4$ and $R^5$ is a hydrogen atom, and the 6-position is an E-form double bond)

The 8-ent-$\Delta^6$-6-fluoro-PGE derivative obtained in Example 21 was reduced in the same manner as in Example 2, and then the removal of a protecting group and the hydrolysis of an ester were conducted in the same manners as described above, to obtain the above identified compound.

$^1$H-NMR: 5.25–5.75(2H, m), 4.97(1H, dd, $J_{HF}$=22 Hz, J=10 Hz).
$^{19}$F-NMR: $-98.4$(dt, J=22, 8 Hz).

27. 8-ent-6-fluoro-PGF$_1$ (a compound of the formula I wherein the 8-position is a R-form, A is a hydroxymethylene group, $R^1$ is a n-pentyl group, and each of $R^2$, $R^3$, $R^4$ and $R^5$ is a hydrogen atom)

The product of Example 26 was subjected to a hydrogenation reaction in the same manner as in Example 3, and then the removal of a protecting group and hydrolysis of an ester were conducted in the same manners as described above to obtain the above identified compound. The product was a mixture of two types of substances which were considered to be epimers at the 6-position.

Low polarity component:
$^1$H-NMR: 5.24–5.70(2H, m), 4.72(1H, dm, $J_{HF}$=51 Hz).
$^{19}$F-NMR: $-180.4$(m).

High polarity component:
$^1$H-NMR: 5.24–5.72(2H, m), 4.62(1H, dm, $J_{HF}$=49 Hz).
$^{19}$F-NMR: $-180.7$(m).

28. 8-ent-6-fluoro-PGE$_1$ (a compound of the formula I wherein the 8-position is a R-form, A is a carbonyl group, $R^1$ is a n-pentyl group, and each of $R^2$, $R^3$, $R^4$ and $R^5$ is a hydrogen atom)

The product of Example 27 was oxidized in the same manner as in Example 4, and the removal of a protecting group and the hydrolysis of an ester were conducted in the same manners as described above to obtain the above identified compound.

Low polarity component:
$^1$H-NMR: 5.24–5.70(2H, m), 4.45(1H, dm, J=50 Hz).
$^{19}$F-NMR: $-185.7$(m).

High polarity component:
$^1$H-NMR: 5.25–5.70(2H, m), 4.40(1H, dm, J=50 Hz).
$^{19}$F-NMR: −181.0(m).

29. (17S)-17,20-dimethyl-6-fluoro-7-hydroxy-PGE$_2$ methyl ester 11,15-bis(t-butyldimethylsilyl ether) (a compound of the formula IV wherein R$^1$ is a (2S)-2-methylhexyl group, R$^2$ is a methyl group, and each of R$^3$ and R$^4$ is a t-butyldimethylsilyl group)

The above identified compound was obtained in a yield of 75% by using (1E,3S,5S)-1-iodo-3-(t-butyldimethylsiloxy)5methyl-1-nonene of (1E,3S)-1-iodo-3-(t-butyldimethylsiloxy)-1-octene in Example 19.

$^1$H-NMR: 5.14(1H, dt, J=22, 8 Hz), 4.69(1H, ddd, J$_{HF}$=27 Hz, J=8, 3 Hz), 3.67(3H, s).
$^{19}$F-NMR: −120.9(dd, J=22, 27 Hz).

In the same manners as described in the foregoing Examples, the following 6-F-17,20-dimethyl-PG derivatives were prepared.

30. (6Z,17S)-Δ$^6$-17,20-dimethyl-6-fluoro-PGF$_1$ (a compound of the formula I wherein A is a hydroxymethylene group, R$^1$ is a (2S)-2-methylhexyl group, each of R$^2$, R$^3$, R$^4$ and R$^5$ is a hydrogen atom, and the 6-position is a Z-form double bond)

$^1$H-NMR: 4.74(1H, dd, J=39, 10 Hz).
$^{19}$F-NMR: −106.9(dt, J=39, 17 Hz).

31. (6E,17S)-8-ent-Δ$^6$-17,20-dimethyl-6-fluoro-PGE$_1$ (a compound of the formula I wherein the 8-position is a R-form, A is a carbonyl group, R$^1$ is a (2S)-2-methylhexyl group, each of R$^2$, R$^3$, R$^4$ and R$^5$ is a hydrogen atom, and the 6-position is an E-form double bond)

$^1$H-NMR: 5.25–5.75(2H, m), 4.79(1H, dd, J$_{HF}$=21 Hz, J=10 Hz).
$^{19}$F-NMR: −99.4(dt, J=21, 8 Hz).

32. (6E,17S)-8-ent-Δ$^6$-17,20-dimethyl-6-fluoro-PGF$_1$ (a compound of the formula I wherein the 8-position is a R-form, A is a hydroxymethylene group, R$^1$ is a (2S)-2-methylhexyl group, each of R$^2$, R$^3$, R$^4$ and R$^5$ is a hydrogen atom, and the 6-position is an E-form double bond)

$^1$H-NMR: 4.79(1H, dd, J$_{HF}$=21 Hz, J=10 Hz).
$^{19}$F-NMR: −99.4(dt, J=21, 8 Hz).

33. (17S)-8-ent-17,20-dimethyl-6-fluoro-PGF$_1$ (a compound of the formula I wherein the 8-position is a R-form, A is a hydroxymethylene group, R$^1$ is a (2S)-2-methylhexyl group, and each of R$^2$, R$^3$, R$^4$ and R$^5$ is a hydrogen atom)

Low polarity component:
$^1$H-NMR: 4.84(1H, dm, J$_{HF}$=51 Hz).
$^{19}$F-NMR: −180.6(m).
High polarity component:
$^1$H-NMR: 4.61(1H, dm, J$_{HF}$=49 Hz).
$^{19}$F-NMR: −183.9(m).

34. (17S)-8-ent-17,20-dimethyl-6-fluoro-PGE$_1$ (a compound of the formula I wherein the 8-position is a R-form, A is a carbonyl group, R$^1$ is a (2S)-2-methylhexyl group, and each of R$^2$, R$^3$, R$^4$ and R$^5$ is a hydrogen atom)

Low polarity component:
$^1$H-NMR: 4.71(1H, dm, J$_{HF}$=49 Hz).
$^{19}$F-NMR: −180.6(m).
High polarity component:
$^1$H-NMR: 4.66(1H, dm, J$_{HF}$=49 Hz).
$^{19}$F-NMR: −180.9(m).

35. (17S)-8-ent-Δ$^2$-17,20-dimethyl-6-fuoro-PGE$_1$ (a compound of the formula I wherein the 8-position is a R-form, A is a carbonyl group, R$^1$ is a (2S)-2-methylhexyl group, each of R$^2$, R$^3$, R$^4$ and R$^5$ is a hydrogen atom, and the 2-position is a double bond)

In the same manner as in Example 16, the low polarity product of 8-ent-17,20-dimethyl-6-fluoro-PGF$_1$ methyl ester 11,15-bis(t-butyldimethylsilyl ether) was treated, and then the hydrolysis of an ester, the Jones oxidation and the desilyl reaction were coducted to obtain the above identified compound.

$^1$H-NMR: 5.08–5.62(2H, m), 4.79(1H, dm, J$_{HF}$=51 Hz).
$^{19}$F-NMR: −180.9(m).

The high polarity component can be converted in the same manner.

PROCESS (C)

36. 9-acetyl-6-hydroxy-PGF$_{1α}$ methyl ester 11,15-bis(t-butyldimethylsilyl ether) (a compound of the formula VII wherein R$^1$ is a n-pentyl group, R$^2$ is a methyl group, each of R$^3$ and R$^4$ is a t-butyldimethylsilyl group, and R$^6$ is an acetyl group)

To a pyridine solution solution (1 ml) of 6-keto-PGF$_{1α}$ methyl ester 11,15-bis(t-butyldimethylsilyl ether) (120 mg, 0.187 mmol), acetic anhydride (1 ml) and 4-dimethylaminopyridine (1.0 mg) were added at 0° C., and the mixture was stirred at 0° C. for 30 minutes and at room temperature for 30 minutes. The reaction solution was poured into a saturated sodium hydrogencarbonate aqueous solution, and the mixture was extracted three times with ethyl ether. The crude product thereby obtained was dissolved in methanol (2 ml), and sodium borohydride (21 mg) was added thereto at 0° C. The mixture was stirred at 0° C. for 30 minutes and then poured into a saturated ammonium chloride aqueous solution. The mixture was extracted with ethyl ether. The organic layer was washed with a saturated sodium chloride aqueous solution, dried and concentrated, and the residue was purified by silica gel column chromatography (ethyl acetate/hexane=1/5) to obtain the above identified compound (121 mg, yield: 95%). The product was a mixture of isomers at the 6-position in a ratio of about 1:1.

Low polarity component:
$^1$H-NMR (CDCl$_3$, TMS): δ2.04(3H, s), 3.53(1H, brs).
High polarity component:
$^1$H-NMR: 2.06(3H, s), 3.52(1H, brs).

This product was converted to a 6-fluoro-PGF$_{1α}$ methyl ester by the following operation.

This 6-hydroxy compound (108 mg, 0.158 mmol) was dissolved in dry methylene chloride (5 ml), and piperidino sulfur trifluoride (0.029 ml) was dropwise added thereto at −78° C. The mixture was stirred at −78° C. for 30 minutes and then diluted with ethyl ether (5 ml), and then it was poured into a saturated sodium hydrogen carbonate aqueous solution cooled with ice. The mixture was extracted with ethyl ether. The organic layer was washed with a saturated sodium chloride aqueous solution, then dried and concentrated.

The residue was dissolved in methanol (5 ml) and anhydrous potassium carbonate (109 mg) was added thereto at 0° C. The mixture was stirred at room temperature for 14 hours. The reaction solution was filtered and washed with ethyl ether. The filtrate was washed with a saturated sodium chloride aqueous solution, then dried and concentrated. The residue was purified by column chromatography (ethyl acetate/hexane=1/5) to obtain the above identified compound (34 mg, yield: 34%). The product was a mixture of isomers at the 6-position in a ratio of about 1:1.

37. (17S)-9-acetyl-17,20-dimethyl-6-hydroxy-PGF$_{1α}$ methyl ester 11,15-bis(t-butyldimethylsilyl ether)

The above identified compound was obtained in a yield of 95% by using (17S)-17,20-dimethyl-6-keto-PGF$_1\alpha$ methyl ester instead of 6-keto-PGF$_1\alpha$ methyl ester 11,15-bis(t-butyldimethylsilyl ether) in Example 36. This product was a mixture of isomers at the 6-position in a ratio of about 1:1.

Low polarity component:
$^1$H-NMR (CDCl$_3$, TMS): δ2.04(3H, s), 3.53(1H, brs).
High polarity component:
$^1$H-NMR: 2.06(3H, s), 3.52(1H, brs).

This compound was also converted to a (17S)-17,20-dimethyl-6-fluoro-PGF$_1$ derivative by subjecting it to a similar process.

FORMULATION EXAMPLE 1

Capsules 50 mg of $\Delta^2$-17S,20-dimethyl-6-fluoro-PGE$_1$ was dissolved in 10 ml of ethanol, and the solution was mixed with 18.5 g of mannitol. The mixture was sieved by a screen of 30 mesh, then dried at 30° C. for 90 minutes and again sieved by a screen of 30 mesh.

To this powder, 200 mg of aerosyl (microfine silica) was added, and the mixture was filled in 100 NO. 3 hard gelatine capsules to obtain a capsule drug containing 0.5 mg of $\Delta^2$-17S,20-methyl-6-fluoro-PGE$_1$ per capsule.

FORMULATION EXAMPLE 2

Injection solution 0.5 mg of $\Delta^2$-17S,20-dimethyl-6-fluoro-PGE$_1$ was dissolved in 5 ml of ethanol. The solution was sterilized by passing it through a bacteria retention filter and introduced into ampoules in an amount of 0.1 ml per ampoule having a capacity of 1 ml so that each ampoule contained 10 μg of $\Delta^2$-17S,20-dimethyl-6-fluoro-PGE$_1$. Then, the ampoules were sealed. The content of each ampoule is to be diluted with a suitable amount of a buffer solution, for example, with 1 ml of a trishydrochloric acid buffer solution of pH 8.6, for use as an injection solution.

FORMULATION EXAMPLE 3

Freeze-dried drug for injection

To a solution comprising 50 mg of $\Delta^2$-17S,20-dimethyl-6-fluoro-PGE$_1$, 1.6 g of α-cyclodextrin and 10 ml of distilled water, 10 mg of citric acid, 50 g of lactose and 800 ml of distilled water were added. The mixture was dissolved and the total amount was adjusted to 1 liter with distilled water. The mixture was then subjected to sterilization filtration in a usual manner and filled in ampoules in an amount of 1 ml per ampoule, followed by freeze drying and sealing to obtain a freeze-dried formulation for injection.

We claim:

1. A 6-fluoroprostaglandin having the formula:

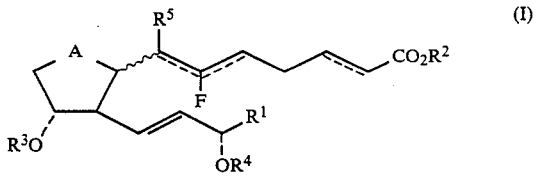

wherein A is a carbonyl group or a hydroxymethylene group, $R^1$ is a straight chain or branched $C_4$–$C_8$ alkyl group, $R^2$ is a hydrogen atom or a $C_1$–$C_{10}$ alkyl group, each of $R^3$ and $R^4$, which may be the same or different, is a hydrogen atom or a protecting group, $R^5$ is a hydrogen atom or a hydroxyl group, and ==== is a single bond or a double bond, and its salt when $R^2$ is a hydrogen atom.

2. The 6-fluoroprostaglandin according to claim 1, wherein $R^1$ is a n-pentyl group or a (2S)-2-methylhexyl group.

3. The 6-fluoroprostaglandin compound according to claim 1, wherein A is a carbonyl group and each of $R^2$, $R^4$ and $R^5$ is a hydrogen atom.

4. The 6-fluoroprostaglandin according to claim 3, wherein each of the 2-, 5- and 6-positions is a single bond.

5. The 6-fluoroprostaglandin according to claim 3, wherein the 2-position is a double bond, and each of the 5- and 6-positions is a single bond.

6. A drug composition having an antiplatelet effect, an antianginal effect or an inhibitory effect on gastric ulcers, which comprises:

a therapeutically effective amount of a 6-fluoroprostaglandin compound having the formula:

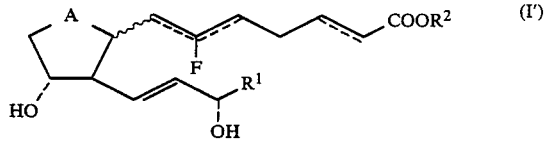

wherein A is a carbonyl group or a hydroxymethylene group, $R^1$ is a straight chain or branched $C_4$–$C_8$ alkyl group, $R^2$ is a hydrogen atom or a $C_1$–$C_{10}$ alkyl group, and ==== represents a single bond or a double bond, or its salt, on a pharmaceutically acceptable carrier.

7. The drug according to claim 6, wherein $R^1$ is a n-pentyl group or a (2S)-2methylhexyl group.

8. The drug according to claim 6, wherein A is a carbonyl group, $R^1$ is a (2S)-2-methylhexyl group, the 2-position is a single bond or a double bond, and each of the 5- and 6-positions is a single bond.

* * * * *